US010745765B2

(12) United States Patent
Ziegler et al.

(10) Patent No.: US 10,745,765 B2
(45) Date of Patent: *Aug. 18, 2020

(54) COMPOSITIONS, METHODS AND KITS TO DETECT ADENOVIRUS NUCLEIC ACIDS

(71) Applicant: GEN-PROBE PRODESSE, INC., San Diego, CA (US)

(72) Inventors: Emily Ziegler, Milwaukee, WI (US); Jessica Townsend, Milwaukee, WI (US)

(73) Assignee: GEN-PROBE PRODESSE, INC., San Diego, CA (US)

( * ) Notice: Subject to any disclaimer, the term of this patent is extended or adjusted under 35 U.S.C. 154(b) by 80 days.

This patent is subject to a terminal disclaimer.

(21) Appl. No.: 16/224,461

(22) Filed: Dec. 18, 2018

(65) Prior Publication Data

US 2019/0218626 A1 Jul. 18, 2019

Related U.S. Application Data

(60) Division of application No. 15/267,615, filed on Sep. 16, 2016, now Pat. No. 10,323,288, which is a continuation of application No. 15/012,096, filed on Feb. 1, 2016, now Pat. No. 9,863,010, which is a continuation of application No. 14/220,466, filed on Mar. 20, 2014, now Pat. No. 9,249,472, which is a division of application No. 13/253,819, filed on Oct. 5, 2011, now Pat. No. 8,715,939.

(51) Int. Cl.
*C12Q 1/70* (2006.01)
*C07H 21/02* (2006.01)
*C07H 21/04* (2006.01)

(52) U.S. Cl.
CPC .............. *C12Q 1/701* (2013.01); *C07H 21/02* (2013.01); *C07H 21/04* (2013.01); *C12Q 2600/158* (2013.01); *C12Q 2600/16* (2013.01)

(58) Field of Classification Search
CPC ..... C12Q 1/701; C12Q 2600/16; C07H 21/04
See application file for complete search history.

(56) References Cited

U.S. PATENT DOCUMENTS

| 8,715,939 | B2* | 5/2014 | Ziegler | ........... C07H 21/02 |
| | | | | 435/6.12 |
| 9,249,472 | B2* | 2/2016 | Ziegler | ........... C07H 21/02 |
| 10,323,288 | B2* | 6/2019 | Ziegler | ........... C07H 21/02 |
| 2003/0215948 | A1 | 11/2003 | Kaleko et al. | |
| 2007/0099177 | A1 | 5/2007 | Heim et al. | |
| 2009/0047665 | A1* | 2/2009 | Hall | ........... C12N 7/00 |
| | | | | 435/5 |
| 2009/0081675 | A1 | 3/2009 | Colston, Jr. et al. | |
| 2009/0118490 | A1 | 5/2009 | Narayanan et al. | |
| 2017/0002430 | A1 | 1/2017 | Ziegler et al. | |

FOREIGN PATENT DOCUMENTS

| ES | 2344443 A1 | 8/2010 |
| WO | 2004099422 A2 | 11/2004 |
| WO | 2005/100611 A2 | 10/2005 |
| WO | 2006063376 A2 | 6/2006 |
| WO | 2007064758 A2 | 6/2007 |
| WO | 20070130519 A2 | 11/2007 |
| WO | 2009009900 A1 | 1/2009 |
| WO | 2009136977 A1 | 11/2009 |
| WO | 2010051367 A2 | 5/2010 |
| WO | 2010097490 A1 | 9/2010 |

OTHER PUBLICATIONS

Damen et al. Real-time PCR with internal control for detection of all known human adenovirus serotypes. J. Clinical Microbiol. (2008) 46:3997-4003.*
USPTO, Examiner-Initiated Interview Summary, U.S. Appl. No. 13/253,819, dated Jul. 30, 2013.
USPTO, Non-Final Office Action, U.S. Appl. No. 13/253,819, dated Sep. 11, 2013.
USPTO, Notice of Allowance, U.S. Appl. No. 13/253,819, dated Jan. 17, 2014.
USPTO, Non-Final Office Actions, U.S. Appl. No. 14/220,466, dated May 28, 2015.
USPTO, Notice of Allowance, U.S. Appl. No. 14/220,466, dated Sep. 25, 2015.
EPO, Communication Pursuant to Rule 94(3) EPC, European Application No. 11796824.8, dated May 8, 2014.
EPO, Communication Pursuant to Rule 94(3) EPC, European Application No. 11796824.8, dated May 29, 2015.
EPO, Communication Pursuant to Rule 94(3) EPC, European Application No. 11796824.8, dated Mar. 22, 2016.
EPO, Communication Pursuant to Rule 94(3) EPC, European Application No. 11796824.8, dated Feb. 28, 2017.
Wong et al: "Detection of a Broad Range of Human Adenoviruses in Respiratory Tract Samples Using a Sensitive Multiplex Real-Time PCR Assay," J. Med. Virol., 2008, 80:856-865, Wiley-Liss Inc., New York City, USA.
Damen et al: "Real-Time PCR with an Internal Control for Detection of All Known Human Adenovirus Serotypes" Journal of Clinical Microbiology. vol. 46. No. 12. Oct. 15, 2008 (Oct. 15, 2008). pp. 3997-4003.
Ebner K et al., "Molecular Detection and Quantitative Analysis of the Entire Spectrum of Human Adenoviruses by a Two-Reaction Real-Time PCR Assay," J. Clin. Microbiol., 2005, 43(7):3049-3053, American Society for Microbiology, Washington D.C., USA.
Ebner K et al: "Comparative Sequence Analysis of the Hexon Gene in the Entire Spectrum of Human Adenovirus Serotypes: Phylogenetic, Taxonomic, and Clinical Implications".J Virol. American Society for Microbiology, US. vol. 79. No. 20. Oct. 1, 2005 (Oct. 1, 2005). pp. 12635-12642.
UKIPO, Examination Report, United Kingdom Patent No. GB1306319. 3, dated Feb. 1, 2017.

(Continued)

*Primary Examiner* — David C Thomas
(74) *Attorney, Agent, or Firm* — Nicholas V. Sherbina; Jeffrey E. Landes

(57) ABSTRACT

The disclosed invention is related to methods, compositions, kits and isolated nucleic acid sequences for targeting Adenovirus nucleic acid. Compositions include amplification oligomers and/or detection probe oligomers. Kits and methods comprise at least one of these oligomers.

20 Claims, No Drawings

Specification includes a Sequence Listing.

(56) References Cited

OTHER PUBLICATIONS

Buckwalter et al., "Real-Time Qualitative PCR for 57 Human Adenovirus Types from Multiple Specimen Sources," J. Clin. Microbiol., 2012, 50(3):776-771, American Society for Microbiology, Washington D.C., USA.
Fabbiani et al., "Epidemiological and Clinical Study of Viral Respiratory Tract Infections in Children From Italy," J. Med. Virol., 2009, 81:750-756, Wiley-Liss Inc., New York City, USA.
German Examination Report, German Patent Application No. 10 2011 120550.4, dated Apr. 16, 2013.
Washington, C. et al. "Multiplexed Luminex xMAP Assay for Detection and Identification of Five Adenovirus Serotypes Associated with Epidemics of Respiratory Disease in Adults." J. Clin. Microbiol. Jun. 2010. vol. 48, No. 6, pp. 2217-2222, electronically published on Apr. 21, 2010.
Database GenBank, Entry No. AB 330090.1 of Jun. 14, 2008.
European patent counsel letter reporting German Decision to Grant a Patent, German Patent Application No. 10 2011 120550.4, dated Jul. 16, 2013.
International Search Report, International Patent Application No. PCT/IB2011/055245, dated Aug. 17, 2012.
Written Opinion, International Patent Application No. PCT/IB2011/055245, dated Apr. 4, 2013.
International Preliminary Report on Patentability, International Patent Application No. PCT/IB2011/055245, dated Apr. 18, 2013.
Gray et al., "Genotype Prevalence and Risk Factors for Severe Clinical Adenovirus Infection, United States 2004-2006," Clin. Infect. Dis., 2007, 45:1120-1131, University of Chicago Press, Chicago, USA.
Gu et al., "Multiplexed, Real-Time PCR for Quantitative Detection of Human Adenovirus," J. Clin. Microbiol., 2003, 41(10):4636-4641, American Society for Microbiology, Washington D.C., USA.
Gustafson et al., "Quantification of adenovirus DNA in unrelated donor hematopoietic stem cell transplant recipients," J. Clin. Virol., 2008, 43:79-85, American Society for Microbiology, Washington D.C., USA.
Heim et al., "Rapid and Quantitative Detection of Human Adenovirus DNA by Real-Time PCR," J. Med. Virol., 2003, 70:228-239, Wiley-Liss Inc., New York City, USA.
Humar et al., "Assessment of Adenovirus Infection in Adult Lung Transplant Recipients Using Molecular Surveillance," The Journal of Heart and Lung Transplantation, 2006, 25(12):1441-1446.
Lee et al., "Comprehensive Serotyping and Epidemiology of Human Adenovirus Isolated From the Respiratory Tract of Korean Children Over 17 Consecutive Years (1991-2007)," Journal of Medical Virology, 2010, 82:624-631, Wiley-Liss Inc., New York City, USA.
Leruez-Ville et al., "Real-Time Blood Plasma Polymerase Chain Reaction for Management of Disseminated Adenovirus Infection," Clin. Infect. Dis., 2004, 38:45-52, The University of Chicago Press, Chicago, USA.
Lu et al., "Molecular typing of human adenoviruses by PCR and sequencing of a partial region of the hexon gene," Arch. Virol., 2006, 151:1587-1602, Springer-Verlag, New York, USA.
Madisch et al., "Phylogenetic Analysis and Structural Predictions of Human Adenovirus Penton Proteins as a Basis for Tissue-Specific Adenovirus Vector Design," J. Virol., 2007, 81(15):8270-8281, American Society for Microbiology, Washington D.C., USA.
Miura-Ochiai et al., "Quantitative Detection and Rapid Identification of Human Adenoviruses," J. Clin. Microbiol., 2007,45(3):958-967, American Society for Microbiology, Washington D.C., USA.
Okada et al., "Detection and sequence-based typing of human adenoviruses using sensitive universal primer sets for the hexon gene," Arch. Virol., 2007, 152:1-9, Springer-Verlag, New York, USA.
Perlman et al., "Quantitative real-time PCR detection of adenovirus in clinical blood specimens: A comparison of plasma, whole blood and peripheral blood mononuclear cells," J. Clin. Virol., 2007, 40:295-300, American Society for Microbiology, Washington D.C., USA.
Pierce et al., "Comparison of the Idaho Technology FilmArray System to Real-Time PCR for Detection of Respiratory Pathogens in Children," J. Clin. Microbiol., 2012, 50(2):364-371, American Society for Microbiology, Washington D.C., USA.
Xu et al., "Species-Specific Identification of Human Adenoviruses by a Multiplex PCR Assay," J. Clin. Microbiol., 2000, 38(11):4114-4120, American Society for Microbiology, Washington D.C., USA.
Prodesse ® ProAdeno™ Package Insert, PIH72 V B, Dec. 2010.
Lowe et al., "A Computer Program for Selection of Oligonucleotide Primers for Polymerase Chain Reactions," Nucleic Acids Research, 1990, vol. 18, No. 7 1757-1761.
UKIPO Search and Examination Report under Sections 17 and 18(3), United Kingdom Application No. GB1721328.1, dated May 8, 2018.
UKIPO Search and Examination Report under Sections 17 and 18(3), United Kingdom Application No. GB1721328.1, dated Mar. 29, 2018.
UKIPO Examination Report, United Kingdom Application No. GB1306319.3, dated Feb. 15, 2018.
EPO Communication pursuant to Article 94(3) EPC, European Application No. 11796824.8, dated Jan. 10, 2018.
UKIPO Examination Report under Section 18(3), United Kingdom Application No. GB1306319.3, dated Dec. 7, 2017.
USPTO Non-Final Office Action, U.S. Appl. No. 15/012,096, dated May 22, 2017.
USPTO Notice of Allowance, U.S. Appl. No. 15/012,096, dated Sep. 7, 2017.
USPTO Non-Final Office Action, U.S. Appl. No. 15/267,615, dated Jul. 5, 2018.
USPTO Notice of Allowance, U.S. Appl. No. 15/267,615, dated Feb. 26, 2019.
EPO Extended European Search Report, European Application No. 18194583.3, dated Nov. 6, 2018.
EPO Article 94(3) EPC Communication, European Application No. 18194583.3, dated May 8, 2020.

* cited by examiner

COMPOSITIONS, METHODS AND KITS TO DETECT ADENOVIRUS NUCLEIC ACIDS

CROSS-REFERENCE TO RELATED APPLICATIONS

This application is a Divisional of U.S. application Ser. No. 15/267,615, filed Sep. 16, 2016, now U.S. Pat. No. 10,323,288, which is a Continuation of U.S. patent application Ser. No. 15/012,096, filed Feb. 1, 2016, now U.S. Pat. No. 9,863,010, which is a Continuation of U.S. patent application Ser. No. 14/220,466, filed Mar. 20, 2014, now U.S. Pat. No. 9,249,472, which is a Divisional of U.S. patent application Ser. No. 13/253,819, filed Oct. 5, 2011, now U.S. Pat. No. 8,715,939; the entire contents of each are incorporated herein by reference in their entirety.

FIELD

The present invention relates to the detection of infectious agents, more specifically to the detection of Adenovirus. Compositions, methods and kits are described for the detection of Adenovirus by using in vitro nucleic acid amplification techniques.

INTRODUCTION

Adenovirus may cause infections in a number of different organs including the gastrointestinal tract, the upper respiratory tract and the eyes. In individuals with a properly functioning immune system, Adenovirus infections are not typically associated with life-threatening disease. However, Adenovirus can cause serious infection in immuno-compromised patients—such as HIV-positive individuals and in patients receiving bone marrow transplants. More than 50 different human Adenovirus serotypes have been identified. On the basis of various properties of Adenovirus, they have been divided into six major subgroups (subgenera or species A-F), with recent literature pointing towards a the presence of a seventh serotype.

Early approaches for detecting Adenovirus detection relied mainly on serological tests and cell culture. In immunosuppressed patients, however, the use of serological tests is limited due to the impaired immune response, and evaluation of positive cultures is a relatively slow method. The introduction of PCR-based assays has provided new methods for the rapid, specific and sensitive detection of Adenovirus. Many of these diagnostic approaches, however, do not effectively cover all Adenovirus serotypes or use low stringency conditions to permit detection of the genetically highly diverse adenoviruses.

The homology of adenovirus DNA sequences between different species is low. Even conserved regions within the Adenovirus genome display only limited homology between adenoviruses from different species. In many instances, considerable differences in DNA sequence even exist between serotypes belonging to the same species. These facts underscore the difficulty to develop molecular tests that facilitate reliable screening for Adenovirus infections with the required broad specificity.

A molecular based assay is required to permit the sensitive and specific detection of multiple adenovirus serotypes.

SUMMARY

It is an object of the present invention to provide methods, compositions and kits that can be used to specifically detect with high sensitivity Adenovirus nucleic acid. Advantageously, the methods, compositions and kits may be used to specifically detect with high sensitivity many (eg. 5 or more, 10 or more, 20 or more, 30 or more, 40 or more or 50 or more), or all known serotypes of adenovirus.

In one aspect, there is provided a method for specifically detecting an Adenovirus target nucleic acid in a sample comprising the steps of: (a) contacting a sample suspected of containing at least an Adenovirus nucleic acid with at least two amplification oligomers for generating an amplicon, wherein each of said at least two amplification oligomers is from 10 to about 50 nucleotides in length and wherein the amplification oligomers are respectively configured to specifically hybridize to regions within a target sequence of Adenovirus selected from the group consisting of from nucleotides 1 to 99 and from nucleotides 83 to 175 of Accession Number AB330090.1 (SEQ ID No. 47); (b) providing conditions sufficient for generating an amplicon from an Adenovirus target nucleic acid present in said sample using said amplification oligomers from step (a); and (c) providing conditions for detecting said amplicon and determining whether an Adenovirus target nucleic acid is present in said sample.

In one embodiment, at least one of said at least two amplification oligomers comprises, consists of consists essentially of a target hybridizing sequence selected from the group consisting of SEQ ID NOS: 1 to 9, 11 to 16, 25 to 28, 31 to 35, 38, and 42 to 46 or a combination of two or more thereof.

In one embodiment, at least one first amplification oligomer comprises, consists of consists essentially of a target hybridizing sequence selected from the group consisting of SEQ ID NOS: 1, 5, 11, 12, 25, 26, 31, 32, 33, 34, 35 or 38 or a combination of two or more thereof.

In one embodiment, at least one second amplification oligomer comprises, consists of consists essentially of a target hybridizing sequence selected from the group consisting of SEQ ID NOS: 2, 3, 6, 7, 8, 9, 13, 14, 15, 16, 27, 28, 42, 43, 44, 45 or 46 or a combination of two or more thereof.

In one embodiment, a first amplification oligomer comprises, consists of consists essentially of a target hybridizing sequence as set forth in SEQ ID NO:1 and at least one second amplification oligomer comprises, consists or consists essentially of SEQ ID NO: 2 and/or SEQ ID NO: 3.

In one embodiment, a first amplification oligomer comprises, consists of consists essentially of a target hybridizing sequence as set forth in SEQ ID NO:5 and at least one second amplification oligomer comprises, consists or consists essentially of a target hybridizing sequence selected from the group consisting of SEQ ID NOS: 6 to 9 or a combination of two or more thereof.

In one embodiment, at least one first amplification oligomer comprises, consists or consists essentially of a target hybridizing sequence as set forth in SEQ ID NO:11 and/or 12 and at least one second amplification oligomer comprises, consists of consists essentially of a target hybridizing sequence selected from the group consisting of SEQ ID NOS: 13 to 16 or a combination of two or more thereof.

In one embodiment, at least one first amplification oligomer comprises, consists of consists essentially of a target hybridizing sequence selected from the group consisting of SEQ ID NO:31 to 35 or 38 or a combination of two or more thereof and at least one second amplification oligomer comprises, consists of consists essentially of a target hybridizing sequence as set forth in SEQ ID NO: 27 and/or 28.

In one embodiment, at least one first amplification oligomer comprises, consists of consists essentially of a target hybridizing sequence as set forth in SEQ ID NO:25 and/or 26 and at least one second amplification oligomer comprises, consists of consists essentially of a target hybridizing sequence as set forth in SEQ ID NO: 27 and/or 28.

In one embodiment, at least two first amplification oligomers each respectively comprise, consist or consist essentially of the target hybridizing sequence as set forth in SEQ ID NO:25 and 26 and at least two second amplification oligomers each respectively comprise, consist or consist essentially of a target hybridizing sequence as set forth in SEQ ID NO: 27 and 28.

In one embodiment, the combination of amplification oligomers is SEQ ID Nos 25, 26, 27 and 28; or SEQ ID Nos 26, 27 and 28; or SEQ ID Nos 25, 26 and 28; or SEQ ID Nos 25, 26 and 27; or SEQ ID Nos 25, 27 and 28; or SEQ ID Nos 25 and 27; or SEQ ID Nos 25 and 28; or SEQ ID Nos 26 and 27; or SEQ ID Nos 26 and 28.

In one embodiment, said detection step comprises contacting said amplification product with at least one detection probe configured to hybridize to a portion of said amplification product.

In one embodiment, the detection probe comprises, consists of consists essentially of a target hybridizing sequence selected from the group consisting of SEQ ID Nos 10, 17 to 24, 29, 30, 36, 37, 39 and 40 or a combination of two or more thereof.

In one embodiment, the detection probe comprises, consists of consists essentially of a sequence as set forth in SEQ ID No. 36 and/or SEQ ID No. 37.

In a further aspect, there is provided a method for detecting an Adenovirus nucleic acid comprising the steps of: (a) contacting a test sample comprising nucleic acid with at least one hybridization assay probe comprising, consisting or consisting essentially of the sequence selected from the group consisting of SEQ ID Nos. 4, 10, 17, 18, 19, 20, 21, 22, 23, 24, 29, 30, 36, 37, 39 and 40 or a combination of two or more thereof; and (b) determining if a probe:target duplex has formed under stringent hybridization conditions in the test sample, wherein the presence of the probe:target duplex is an indication of the presence of Adenovirus nucleic acid in the test sample.

In a further aspect, there is provided a composition for use in an Adenovirus target nucleic acid amplification assay comprising at least two amplification oligomers capable of stably hybridizing to Adenovirus target nucleic acid, wherein each of said at least two amplification oligomers is from 10 to about 50 nucleotides in length and wherein the amplification oligomers are respectively configured to specifically hybridize to regions within a target sequence of Adenovirus selected from the group consisting of from nucleotides 1 to 99 and from nucleotides 83 to 175 of Accession Number AB330090.1 (SEQ ID No. 47).

At least one first amplification oligomer comprises, consists of consists essentially of a target hybridizing sequence as set forth in SEQ ID NO:25 and/or SEQ ID NO:26 and wherein at least one second amplification oligomer comprises, consists of consists essentially of a target hybridizing sequence as set forth in SEQ ID NO:27 and/or SEQ ID NO:28.

In one embodiment, the first and second amplification oligomers are selected from the group consisting of SEQ ID Nos 25, 26, 27 and 28; SEQ ID Nos 26, 27 and 28; SEQ ID Nos 25, 26 and 28; SEQ ID Nos 25, 26 and 27; SEQ ID Nos 25, 27 and 28; SEQ ID Nos 25 and 27; SEQ ID Nos 25 and 28; SEQ ID Nos 26 and 27 and SEQ ID Nos 26 and 28 or a combination of two or more thereof.

In one embodiment, the composition further comprises a detection probe.

In one embodiment, the detection probe comprises, consists of consists essentially of a sequence selected from the group consisting of SEQ ID Nos 10, 17 to 24, 29, 30, 36, 37, 39 and 40 or a combination of two or more thereof.

In one embodiment, the detection probe comprises, consists of consists essentially of a sequence as set forth in SEQ ID No. 36 and/or SEQ ID No. 37.

In a further aspect, there is provided a kit comprising the composition of the present invention and optionally a set of instructions for performing same.

In a further aspect, there is provided an isolated DNA sequence substantially corresponding to the sequence set forth in any of SEQ ID Nos: 1 to 46 or the corresponding isolated RNA sequence.

In one embodiment, said sequence is the complement or the reverse complement thereof.

In a further aspect, there is provided the use of the isolated DNA sequence for amplifying and/or detecting Adenovirus nucleic acid.

DETAILED DESCRIPTION

Nucleic acid oligomer sequences are disclosed that may serve as primers and/or detection probes for amplification and/or detection of Adenovirus nucleic acids. The Adenovirus nucleic acids may be detected in a sample by using methods of in vitro nucleic acid amplification—such as PCR (eg. Taqman PCR)—or transcription-mediated amplification—such as TMA or NASBA. Probes for detection of the amplified nucleic acid sequences are also described. Detection probes hybridize specifically to at least a portion of the amplified sequence, either after completion of or during the amplification process. Some embodiments detect the amplified products by using a homogeneous detection method that detects, in a mixture, a labeled probe bound specifically to an amplified sequence (eg., see Arnold et al., 1989, *Clin. Chem.* 35:1588-1594; U.S. Pat. No. 5,658,737, Nelson et al., and U.S. Pat. Nos. 5,118,801 and 5,312,728, Lizardi et al.). The methods may use oligonucleotide sequences that serve as capture probes for processing a sample to capture the target Adenovirus nucleic acid and separate it from other sample components (e.g. see U.S. Pat. Nos. 6,110,678, 6,280,952 and 6,534,273).

Methods disclosed herein can be used to detect Adenovirus nucleic acids present in samples from or derived from animals and humans.

Compositions disclosed herein include amplification oligomers that can be used to specifically amplify selected nucleic acid sequences present in Adenovirus genomic sequences, and optionally nucleic acid probes for detecting the amplified sequences.

The disclosed nucleic acid sequences and methods are useful for amplifying and detecting Adenovirus nucleic acids from or derived from viral particles present in a sample in a relatively short time so that diagnosis can be made quickly and so effective treatment can be initiated and spread of the virus limited. The methods are useful for screening for individuals who have Adenovirus infections but who do not exhibit definitive symptoms and are particularly useful for screening patients who have a higher risk of death or serious complications from Adenovirus infections, eg., the young, elderly, or immunocompromised individuals. The methods are also useful for rapid screening of many samples. The methods are useful because they minimize the risk of exposure of laboratory personnel to the infectious Adenovirus agents, thereby limiting the risk of infection and spread of the virus. Thus, the methods and compositions disclosed herein respond to a need for rapid, sensitive, and specific testing of clinical samples that may contain Adenovirus.

The disclosed probe sequences may be used as primers, and the disclosed primers may be used as probes. The same is true for the disclosed probe domains and primer domains. Thus, the probe domains disclosed herein may be used as primer domains. Likewise, primer domains disclosed herein may be used as probe domains.

The amplification oligomers disclosed herein are further contemplated as components of multiplex amplification reactions wherein several amplicon species that can be produced from an assortment (eg. two or more, three or more, for or more, five or more, six or more, or even ten or more) of target-specific primers. For example, it is contemplated that more than one of the amplification systems disclosed herein can be combined to result in a multiplex assay that is both robust and broad in its capacity for target detection—such as the ability to detect 5 or more, 10 or more, 20 or more, 30 or more, 40 or more or 50 or more, or all known serotypes of adenovirus.

To aid in understanding aspects of the disclosure, some terms used herein are described in more detail. All other scientific and technical terms used herein have the same meaning as commonly understood by those skilled in the relevant art, such as may be provided in *Dictionary of Microbiology and Molecular Biology,* 2nd ed. (Singleton et al., 1994, John Wiley & Sons, New York, N.Y.), *The Harper Coffins Dictionary of Biology* (Hale & Marham, 1991, Harper Perennial, New York, N.Y.), and references cited herein. Unless mentioned otherwise, the techniques employed or contemplated herein are standard methods well known to a person of ordinary skill in the art of molecular biology.

It is to be noted that the term "a" or "an" entity refers to one or more of that entity; for example, "a nucleic acid," is understood to represent one or more nucleic acids. As such, the terms "a" (or "an"), "one or more," and "at least one" can be used interchangeably herein.

Sample. A "sample" or "specimen", including "biological" or "clinical" samples may contain or may be suspected of containing Adenovirus or components thereof, such as nucleic acids or fragments of nucleic acids. A sample may be a complex mixture of components. Samples include "biological samples" which include any tissue or material derived from a living or dead mammal or organism, including, for example, blood, plasma, serum, blood cells, saliva, mucous and cerebrospinal fluid. Samples may also include samples of in vitro cell culture constituents including, eg., conditioned media resulting from the growth of cells and tissues in culture medium. The sample may be treated to physically or mechanically disrupt tissue or cell structure to release intracellular nucleic acids into a solution which may contain enzymes, buffers, salts, detergents and the like, to prepare the sample for analysis. In one step of the methods described herein, a sample is provided that is suspected of containing at least an Adenovirus target nucleic acid. Accordingly, this step excludes the physical step of obtaining the sample from a subject.

Nucleic acid. This refers to a multimeric compound comprising two or more covalently bonded nucleosides or nucleoside analogs having nitrogenous heterocyclic bases, or base analogs, where the nucleosides are linked together by phosphodiester bonds or other linkages to form a polynucleotide. Nucleic acids include RNA, DNA, or chimeric DNA-RNA polymers or oligonucleotides, and analogs thereof. A nucleic acid "backbone" may be made up of a variety of linkages, including one or more of sugar-phosphodiester linkages, peptide-nucleic acid bonds (in "peptide nucleic acids" or PNAs, see PCT No. WO 95/32305), phosphorothioate linkages, methylphosphonate linkages, or combinations thereof. Sugar moieties of the nucleic acid may be either ribose or deoxyribose, or similar compounds having known substitutions, e.g., 2' methoxy substitutions and 2' halide substitutions (e.g., 2'-F). Nitrogenous bases may be conventional bases (A, G, C, T, U), analogs thereof (e.g., inosine, 5-methylisocytosine, isoguanine; *The Biochemistry of the Nucleic Acids* 5-36, Adams et al., ed., 11th ed., 1992, Abraham et al., 2007, BioTechniques 43: 617-24), which include derivatives of purine or pyrimidine bases (e.g., $N^4$-methyl deoxygaunosine, deaza- or aza-purines, deaza- or aza-pyrimidines, pyrimidine bases having substituent groups at the 5 or 6 position, purine bases having an altered or replacement substituent at the 2, 6 and/or 8 position, such as 2-amino-6-methylaminopurine, $O^6$-methylguanine, 4-thio-pyrimidines, 4-amino-pyrimidines, 4-dimethylhydrazine-pyrimidines, and $O^4$-alkyl-pyrimidines, and pyrazolo-compounds, such as unsubstituted or 3-substituted pyrazolo[3,4-d]pyrimidine; U.S. Pat. Nos. 5,378,825, 6,949,367 and PCT No. WO 93/13121). Nucleic acids may include "abasic" residues in which the backbone does not include a nitrogenous base for one or more residues (U.S. Pat. No. 5,585,481). A nucleic acid may comprise only conventional sugars, bases, and linkages as found in RNA and DNA, or may include conventional components and substitutions (e.g., conventional bases linked by a 2' methoxy backbone, or a nucleic acid including a mixture of conventional bases and one or more base analogs). Nucleic acids may include "locked nucleic acids" (LNA), in which one or more nucleotide monomers have a bicyclic furanose unit locked in an RNA mimicking sugar conformation, which enhances hybridization affinity toward complementary sequences in single-stranded RNA (ssRNA), single-stranded DNA (ssDNA), or double-stranded DNA (dsDNA) (Vester et al., 2004, *Biochemistry* 43(42):13233-41). Nucleic acids may include modified bases to alter the function or behaviour of the nucleic acid, e.g., addition of a 3'-terminal dideoxynucleotide to block additional nucleotides from being added to the nucleic acid. Synthetic methods for making nucleic acids in vitro are well known in the art although nucleic acids may be purified from natural sources using routine techniques.

Polynucleotide. The term denotes a nucleic acid chain. Throughout this application, nucleic acids are designated by the 5'-terminus to the 3'-terminus. Standard nucleic acids, e.g., DNA and RNA, are typically synthesized "3'-to-5'," i.e., by the addition of nucleotides to the 5'-terminus of a growing nucleic acid.

Nucleotide. This is a subunit of a nucleic acid consisting of a phosphate group, a 5-carbon sugar and a nitrogenous base. The 5-carbon sugar found in RNA is ribose. In DNA, the 5-carbon sugar is 2'-deoxyribose. The term also includes analogs of such subunits, such as a methoxy group at the 2' position of the ribose (2'-O-Me, or 2' methoxy). As used herein, methoxy oligonucleotides containing "T" residues have a methoxy group at the 2' position of the ribose moiety, and a uracil at the base position of the nucleotide.

Non-nucleotide unit. This is a unit that does not significantly participate in hybridization of a polymer. Such units must not, for example, participate in any significant hydrogen bonding with a nucleotide, and would exclude units having as a component one of the five nucleotide bases or analogs thereof.

Target nucleic acid. This is a nucleic acid comprising a "target sequence" to be amplified. Target nucleic acids may be DNA or RNA and may be either single-stranded or double-stranded. In a preferred embodiment of the invention, the target nucleic acid is DNA. The target nucleic acid may include other sequences besides the target sequence that may be amplified. Typical target nucleic acids are or are derived from the Adenovirus genome.

Target sequence. This term refers to the particular nucleotide sequence of the target nucleic acid that is to be amplified. Where the target nucleic acid is originally single-stranded, the term "target sequence" will also refer to the sequence complementary to the target sequence as present in the target nucleic acid. Where the target nucleic acid is originally double-stranded, the term "target sequence" refers to both the sense (+) and antisense (−) strands. In choosing a target sequence, the skilled artisan will understand that a sequence should be chosen so as to distinguish between unrelated or closely related target nucleic acids. The terms "target(s) a sequence" or "target(s) a target nucleic acid" as used herein in reference to a region of Adenovirus nucleic acid refers to a process whereby an oligonucleotide stably hybridizes to the target sequence in a manner that allows for amplification and/or detection as described herein. In one embodiment, the oligonucleotide is complementary to the targeted Adenovirus nucleic acid sequence and contains no mismatches. In another embodiment, the oligonucleotide is complementary but contains 1; or 2; or 3; or 4; or 5 or more mismatches with the targeted Adenovirus nucleic acid sequence. Preferably, the oligonucleotide that stably hybridizes to the Adenovirus nucleic acid sequence includes at least 10, 11, 12, 13, 14, 15, 16, 17, 18, 19, 20, 21, 22, 23, 24, 25, 30, 35, 40, 45 or 50 contiguous nucleotides complementary to the target sequence. It is understood that at least 10 and as many as 50 is an inclusive range such that 10, 50 and each whole number there between are included. The term "configured to target a sequence" as used herein means that the target hybridizing region of an amplification oligonucleotide is designed to have a polynucleotide sequence that could target a sequence of the referenced Adenovirus region. Such an amplification oligonucleotide is not limited to targeting that sequence only, but is rather useful as a composition, in a kit or in a method for targeting an Adenovirus target nucleic acid, as is described herein. The term "configured to" denotes an actual arrangement of the polynucleotide sequence configuration of the amplification oligonucleotide target hybridizing sequence.

Isolated. This is meant that a nucleic acid is taken from its natural milieu, but the term does not connote any degree of purification.

Fragment. This term as used herein in reference to the Adenovirus targeted nucleic acid sequence refers to a piece of contiguous nucleic acid. In certain embodiments, the fragment includes contiguous nucleotides from Adenovirus target nucleic acid, wherein the number of contiguous nucleotides in the fragment are less than that for the entire Adenovirus genome or a gene thereof.

Region. This term refers to a portion of a nucleic acid wherein said portion is smaller than the entire nucleic acid. For example, when the nucleic acid in reference is an oligonucleotide promoter provider, the term "region" may be used refer to the smaller promoter portion of the entire oligonucleotide. Similarly, and also as example only, when the nucleic acid is a target nucleic acid, the term "region" may be used to refer to a smaller area of the nucleic acid.

Oligonucleotide. This term may be used interchangeably with "oligomer and "oligo" and refers to a nucleic acid having generally less than 1,000 nucleotide (nt) residues, including polymers in a range of from about 5 nt residues to about 900 nt residues, from about 10 nt residues to about 800 nt residues with a lower limit of about 12 to 15 nt and an upper limit of about 40 to 600 nt, and other embodiments are in a range having a lower limit of about 15 to 20 nt and an upper limit of about 22 to 100 nt. It is understood that these ranges are exemplary only, and an oligonucleotide may contain each whole number included in the range. Oligonucleotides may be purified from naturally occurring sources, but may be synthesized using any of a variety of well-known enzymatic or chemical methods. The term oligonucleotide does not denote any particular function to the reagent; rather, it is used generically to cover all such reagents described herein. An oligonucleotide may serve various different functions. For example, it may function as a primer if it is specific for and capable of hybridizing to a complementary strand and can further be extended in the presence of a nucleic acid polymerase, it may provide a promoter if it contains a sequence recognized by an RNA polymerase and allows for transcription (eg., a T7 provider), and it may function to prevent hybridization or impede primer extension if appropriately situated and/or modified.

As used herein, an oligonucleotide having a nucleic acid sequence "comprising" or "consisting of" or "consisting essentially of" a sequence selected from a group of specific sequences means that the oligonucleotide, as a basic and novel characteristic, is capable of stably hybridizing to a nucleic acid having the exact complement of one of the listed nucleic acid sequences of the group under stringent hybridization conditions. An exact complement includes the corresponding DNA or RNA sequence.

Corresponds. As used herein, a nucleic acid "corresponds" to a specified nucleic acid if the nucleic acid is 100% identical or complementary to the specified nucleic acid.

Substantially corresponding to. As used herein, a nucleic acid "substantially corresponding to" a specified nucleic acid sequence means that the referred to oligonucleotide is sufficiently similar to the reference nucleic acid sequence such that the oligonucleotide has similar hybridization properties to the reference nucleic acid sequence in that it would hybridize with the same target nucleic acid sequence under stringent hybridization conditions. Substantially corresponding nucleic acids vary by at least one nucleotide from the specified nucleic acid. This variation may be stated in terms of a percentage of identity or complementarity between the nucleic acid and the specified nucleic acid. Thus, nucleic acid substantially corresponds to a reference nucleic acid sequence if these percentages of base identity or complementarity are from less than 100% to about 80%. In preferred embodiments, the percentage is at least about 85%. In more preferred embodiments, this percentage is at least about 90%; in other preferred embodiments, this percentage is at least about 95%, 96%, 97%, 98% or 99%. One skilled in the art will understand that the recited ranges include all whole and rational numbers of the range (e.g., 92% or 92.377%).

Helper oligonucleotide. A "helper oligonucleotide" or "helper" refers to an oligonucleotide designed to bind to a target nucleic acid and impose a different secondary and/or tertiary structure on the target to increase the rate and extent of hybridization of a detection probe or other oligonucleotide with the targeted nucleic acid, as described, for example, in U.S. Pat. No. 5,030,557. Helpers may also be used to assist with the hybridization to target nucleic acid sequences and function of primer, target capture and other oligonucleotides. Helper oligonucleotides may be used in the methods described herein and may form part of the compositions and kits described herein.

Blocking moiety. As used herein, a "blocking moiety" is a substance used to "block" the 3'-terminus of an oligonucleotide or other nucleic acid so that it cannot be efficiently extended by a nucleic acid polymerase.

Amplification oligomer. An "amplification oligomer", which may also be called an "amplification oligonucleotide" is an oligomer, at least the 3'-end of which is complementary to a target nucleic acid ("target hybridizing sequence"), and which hybridizes to a target nucleic acid, or its complement, and participates in a nucleic acid amplification reaction. An example of an amplification oligomer is a "primer" that hybridizes to a target nucleic acid and contains a 3' OH end that is extended by a polymerase in an amplification process. Another example of an amplification oligomer is a "promoter-based amplification oligomer," which comprises a target hybridizing sequence, and a promoter sequence for initiating transcription by an appropriate polymerase. Promoter-based amplification oligomers may or may not be extended by a polymerase in a primer-based extension depending upon whether or not the 3' end of the target hybridizing sequence is modified to prevent primer-based extension (e.g., a 3' blocked end). A promoter-based amplification oligonucleotide comprising a target hybridizing region that is not modified to prevent primer-based extension is referred to as a "promoter-primer." A promoter-based amplification oligonucleotide comprising a target hybridizing region that is modified to prevent primer-based extension is referred to as a "promoter-provider." Size ranges for amplification oligonucleotides include those comprising target hybridizing regions that are about 10 to about 70 nt long—such as about 10 to about 60 nt long, about 10 to about 50 nt long, about 10 to about 40 nt long, about 10 to about 30 nt long or about 10 to about 25 nt long or about 15 to 25 nt long. Preferred sizes of amplification oligomers include those comprising target hybridizing regions that are about 18, 19, 20, 21, 22 or 23 nt long. An amplification oligomer may optionally include modified nucleotides or analogs that are not complementary to target nucleic acid in a strict A:T/U, G:C sense. Such modified nucleotides or analogs are herein considered mismatched to their corresponding target sequence.

Oligomers not intended for primer-based extension by a nucleic acid polymerase may include a blocker group that replaces the 3'OH to prevent the enzyme-mediated extension of the oligomer in an amplification reaction. For example, blocked amplification oligomers and/or detection probes present during amplification may not have functional 3'OH and instead include one or more blocking groups located at or near the 3' end. In some embodiments a blocking group near the 3' end and may be within five residues of the 3' end and is sufficiently large to limit binding of a polymerase to the oligomer. In other embodiments a blocking group is covalently attached to the 3' terminus. Many different chemical groups may be used to block the 3' end, e.g., alkyl groups, non-nucleotide linkers, alkane-diol dideoxynucleotide residues, and cordycepin.

Promoter. This refers to a specific nucleic acid sequence that is recognized by a DNA-dependent RNA polymerase ("transcriptase") as a signal to bind to the nucleic acid and begin the transcription of RNA at a specific site.

Promoter-provider. As used herein, a "promoter-provider" or "provider" refers to an oligonucleotide comprising first and second regions, and which is modified to prevent the initiation of DNA synthesis from its 3'-terminus. The "first region" of a promoter—provider oligonucleotide comprises a base sequence which hybridizes to a DNA template, where the hybridizing sequence is situated 3', but not necessarily adjacent to, a promoter region. The target-hybridizing portion of a promoter oligonucleotide is typically at least 10, 11, 12, 13, 14, 15, 16, 17, 18, 19, 20, 21, 22, 23, 24, 25, 30, 35, 40 or 45 nucleotides in length, and may extend up to 50 or more nucleotides in length. The "second region" comprises a promoter sequence for an RNA polymerase. A promoter-provider oligonucleotide is configured so that it is incapable of being extended by an RNA- or DNA-dependent DNA polymerase, (e.g., reverse transcriptase), preferably by comprising a blocking moiety at its 3'-terminus as described above. This modification differentiates promoter providers from promoter primers. Preferably, the promoter portion of a promoter primer or provider is a promoter for a DNA-dependent RNA polymerase from *E. coli* and bacteriophages T7, T3, and SP6, though other promoters or modified version thereof can be used as well.

Terminating oligonucleotide. As used herein, a "terminating oligonucleotide" or "blocker oligonucleotide" is an oligonucleotide comprising a base sequence that is complementary to a region of the target nucleic acid in the vicinity of the 5'-end of the target sequence, so as to "terminate" primer extension of a nascent nucleic acid that includes a priming oligonucleotide, thereby providing a defined 3'-end for the nascent nucleic acid strand.

Amplification. This refers to any known procedure for obtaining multiple copies of a target nucleic acid sequence or its complement or fragments thereof. The multiple copies may be referred to as amplicons or amplification products. Amplification of "fragments" refers to production of an amplified nucleic acid that contains less than the complete target nucleic acid or its complement, eg., produced by using an amplification oligonucleotide that hybridizes to, and initiates polymerization from, an internal position of the target nucleic acid. Known amplification methods include both thermal and isothermal amplification methods. For some embodiment, isothermal amplification methods are preferred. Replicase-mediated amplification, polymerase chain reaction (PCR), ligase chain reaction (LCR), strand-displacement amplification (SDA), and transcription-mediated or transcription-associated amplification are non-limiting examples of nucleic acid amplification methods. Replicase-mediated amplification uses self-replicating RNA molecules, and a replicase such as QB-replicase (eg., U.S. Pat. No. 4,786,600). PCR amplification uses a DNA polymerase, pairs of primers, and thermal cycling to synthesize multiple copies of two complementary strands of dsDNA or from a cDNA (eg., U.S. Pat. Nos. 4,683,195, 4,683,202, and 4,800,159). LCR amplification uses four or more different oligonucleotides to amplify a target and its complementary strand by using multiple cycles of hybridization, ligation, and denaturation (eg., U.S. Pat. Nos. 5,427,930 and 5,516, 663). SDA uses a primer that contains a recognition site for a restriction endonuclease and an endonuclease that nicks one strand of a hemimodified DNA duplex that includes the target sequence, whereby amplification occurs in a series of primer extension and strand displacement steps (eg., U.S. Pat. Nos. 5,422,252; 5,547,861; and 5,648,211).

Transcription associated amplification. This method of amplification, also referred to herein as "transcription mediated amplification" (TMA) refers to nucleic acid amplification that uses an RNA polymerase to produce multiple RNA transcripts from a nucleic acid template. These methods generally employ an RNA polymerase, a DNA polymerase, deoxyribonucleoside triphosphates, ribonucleoside triphosphates, and a template complementary oligonucleotide that includes a promoter sequence, and optionally may include one or more other oligonucleotides. TMA methods are embodiments of amplification methods used for amplifying and detecting Adenovirus target sequences as described herein. Variations of transcription associated amplification are well known in the art as previously disclosed in detail (eg., U.S. Pat. Nos. 4,868,105; 5,124,246; 5,130,238; 5,399,491; 5,437,990; 5,554,516; and 7,374,885; and PCT Pub. Nos. WO 88/01302; WO 88/10315 and WO 95/03430). The person of ordinary skill in the art will appreciate that the disclosed compositions may be used in amplification methods based on extension of oligomer sequences by a polymerase.

Real-time amplification. As used herein, the term "real-time amplification" refers to amplification of target nucleic acid that is monitored by real-time detection means.

Amplicon. This term, which is used interchangeably with "amplification product", refers to the nucleic acid molecule generated during an amplification procedure that is complementary or homologous to a sequence contained within the target sequence. These terms can be used to refer to a single strand amplification product, a double strand amplification product or one of the strands of a double strand amplification product.

Probe. A probe, also known as a "detection probe" or "detection oligonucleotide" are terms referring to a nucleic acid oligomer that hybridizes specifically to a target sequence in a nucleic acid, or in an amplified nucleic acid, under conditions that promote hybridization to allow detection of the target sequence or amplified nucleic acid. Detection may either be direct (e.g., a probe hybridized directly to its target sequence) or indirect (e.g., a probe linked to its target via an intermediate molecular structure). Probes may be DNA, RNA, analogs thereof or combinations thereof and they may be labeled or unlabeled. A probe's "target sequence" generally refers to a smaller nucleic acid sequence within a larger nucleic acid sequence that hybridizes specifically to at least a portion of a probe oligomer by standard base pairing. A probe may comprise target-specific sequences and other sequences that contribute to the three-dimensional conformation of the probe (eg., U.S. Pat. Nos. 5,118,801; 5,312,728; 6,849,412; 6,835,542; 6,534,274; and 6,361,945; and US Pub. No. 20060068417). In a preferred embodiment, the detection probe comprises a 2' methoxy backbone which can result in a higher signal being obtained. In another preferred embodiment, the probe comprises a fluorophore covalently attached to the 5'-end of the probe and a quencher at the 3'-end. Such probes are known as Taqman probes.

Stable. By "stable" or "stable for detection" is meant that the temperature of a reaction mixture is at least 2.deg. C. below the melting temperature of a nucleic acid duplex.

Label. As used herein, a "label" refers to a moiety or compound joined directly or indirectly to a probe that is detected or leads to a detectable signal. Direct labeling can occur through bonds or interactions that link the label to the probe, including covalent bonds or non-covalent interactions, e.g. hydrogen bonds, hydrophobic and ionic interactions, or formation of chelates or coordination complexes. Indirect labeling can occur through use of a bridging moiety or "linker" such as a binding pair member, an antibody or additional oligomer, which is either directly or indirectly labeled, and which may amplify the detectable signal. Labels include any detectable moiety, such as a radionuclide, ligand (e.g., biotin, avidin), enzyme or enzyme substrate, reactive group, or chromophore (e.g., dye, particle, or bead that imparts detectable color), luminescent compound (e.g., bioluminescent, phosphorescent, or chemiluminescent labels), or fluorophore. Labels may be detectable in a homogeneous assay in which bound labeled probe in a mixture exhibits a detectable change different from that of an unbound labeled probe, e.g., instability or differential degradation properties. A "homogeneous detectable label" can be detected without physically removing bound from unbound forms of the label or labeled probe (e.g., U.S. Pat. Nos. 5,283,174, 5,656,207, and 5,658,737). Labels include chemiluminescent compounds, e.g., acridinium ester ("AE") compounds that include standard AE and derivatives (e.g., U.S. Pat. Nos. 5,656,207, 5,658,737, and 5,639,604). Synthesis and methods of attaching labels to nucleic acids and detecting labels are well known (e.g., Sambrook et al., *Molecular Cloning, A Laboratory Manual,* 2nd ed. (Cold Spring Harbor Laboratory Press, Cold Spring Harbor, N.Y., 1989), Chapter 10; U.S. Pat. Nos. 5,658,737, 5,656,207, 5,547,842, 5,283,174, and 4,581,333). More than one label, and more than one type of label, may be present on a particular probe, or detection may use a mixture of probes in which each probe is labeled with a compound that produces a different detectable signal (e.g., U.S. Pat. Nos. 6,180,340 and 6,350,579).

Molecular torches. As used herein, structures referred to as "molecular torches" are designed to include distinct regions of self-complementarity ("the closing domain") which are connected by a joining region ("the target binding domain") and which hybridize to one another under predetermined hybridization assay conditions. All or part of the nucleotide sequences comprising target closing domains may also function as target binding domains. Thus, target closing sequences can include, target binding sequences, non-target binding sequences, and combinations thereof.

Capture oligonucleotide. As used herein, a "capture oligonucleotide," "target capture oligonucleotide" or "capture probe" refers to a nucleic acid oligomer that specifically hybridizes to a target sequence in a target nucleic acid by standard base pairing and joins to a binding partner on an immobilized probe to capture the target nucleic acid to a support. One example of a capture oligomer includes an oligonucleotide comprising two binding regions: a target hybridizing sequence and an immobilized probe-binding region. A variation of this example, the two regions may be present on two different oligomers joined together by one or more linkers. Another embodiment of a capture oligomer the target hybridizing sequence is a sequence that includes random or non-random poly-GU, poly-GT, or poly U sequences to bind non-specifically to a target nucleic acid and link it to an immobilized probe on a support. (PCT Pub No. WO 2008/016988). The immobilized probe binding region can be a nucleic acid sequence, referred to as a tail. Tails include a substantially homopolymeric tail of about 10 to 40 nucleotides (e.g., $A_{10}$ to $A_{40}$), or of about 14 to 33 nt (e.g., $T_3A_{14}$ to $T_3A_{30}$), that bind to a complementary immobilized sequence attached to the support particle or support matrix. Thus, a non-limiting example of preferred nucleic acid tails can in some embodiments include $T_{0-4}A_{10-36}$ sequences. Another example of a capture oligomer comprises two regions, a target hybridizing sequence and a binding pair member that is not a nucleic acid sequence.

Immobilized oligonucleotide. As used herein, an "immobilized oligonucleotide", "immobilized probe" or "immobilized nucleic acid" refers to a nucleic acid binding partner that joins a capture oligomer to a support, directly or indirectly. An immobilized probe joined to a support facilitates separation of a capture probe bound target from unbound material in a sample. One embodiment of an immobilized probe is an oligomer joined to a support that facilitates separation of bound target sequence from unbound material in a sample. Supports may include known materials, such as matrices and particles free in solution, which may be made of nitrocellulose, nylon, glass, polyacrylate, mixed polymers, polystyrene, silane, polypropylene, metal, or other compositions, of which one embodiment is magnetically attractable particles. Supports may be monodisperse magnetic spheres (e.g., uniform size ±5%), to which an immobilized probe is joined directly (via covalent linkage, chelation, or ionic interaction), or indirectly (via one or more linkers), where the linkage or interaction between the probe and support is stable during hybridization conditions.

Complementary. By "complementary" is meant that the nucleotide sequences of similar regions of two single-stranded nucleic acids, or to different regions of the same single-stranded nucleic acid have a nucleotide base composition that allow the single-stranded regions to hybridize together in a stable double-stranded hydrogen-bonded region under stringent hybridization or amplification conditions. Sequences that hybridize to each other may be completely complementary or partially complementary to the intended target sequence by standard nucleic acid base pairing (e.g. G:C, A:T or A:U pairing). By "sufficiently complementary" is meant a contiguous sequence that is capable of hybridizing to another sequence by hydrogen bonding between a series of complementary bases, which may be complementary at each position in the sequence by standard base pairing or may contain one or more residues that are not complementary by standard A:T/U and G:C pairing, or are modified nucleotides such as abasic residues, modified nucleotides or nucleotide analogs. Sufficiently complementary contiguous sequences typically are at least 80%, or at least 90%, complementary to a sequence to which an oligomer is intended to specifically hybridize (a %-complementarity range includes all whole and rational numbers of the range). Sequences that are "sufficiently complementary" allow stable hybridization of a nucleic acid oligomer with its target sequence under appropriate hybridization conditions, even if the sequences are not completely complementary. When a contiguous sequence of nucleotides of one single-stranded region is able to form a series of "canonical" hydrogen-bonded base pairs with an analogous sequence of nucleotides of the other single-stranded region, such that A is paired with U or T and C is paired with G, the nucleotides sequences are "completely" complementary.

Preferentially hybridize. By "preferentially hybridize" is meant that under stringent hybridization assay conditions, an oligonucleotide hybridizes to its target sequences, or replicates thereof, to form stable oligonucleotide: target sequence hybrid, while at the same time formation of stable oligonucleotide: non-target sequence hybrid is minimized. For example, a probe oligonucleotide preferentially hybridizes to a target sequence or replicate thereof to a sufficiently greater extent than to a non-target sequence, to enable one having ordinary skill in the art to accurately detect the RNA replicates or complementary DNA (cDNA) of the target sequence formed during the amplification. Appropriate hybridization conditions are well known in the art for probe, amplification, target capture, blocker and other oligonucleotides, may be predicted based on sequence composition, or can be determined by using routine testing methods (e.g., Sambrook et al., *Molecular Cloning, A Laboratory Manual*, 2nd ed. (Cold Spring Harbor Laboratory Press, Cold Spring Harbor, N.Y., 1989) at §§ 1.90-1.91, 7.37-7.57, 9.47-9.51 and 11.47-11.57, particularly §§ 9.50-9.51, 11.12-11.13, 11.45-11.47 and 11.55-11.57).

Nucleic acid hybrid. By "nucleic acid hybrid" or "hybrid" or "duplex" is meant a nucleic acid structure containing a double-stranded, hydrogen-bonded region wherein each strand is complementary to the other, and wherein the region is sufficiently stable under stringent hybridization conditions to be detected by means including, but not limited to, chemiluminescent or fluorescent light detection, autoradiography, or gel electrophoresis. Such hybrids may comprise RNA:RNA, RNA:DNA, or DNA:DNA duplex molecules.

Sample preparation. This refers to any steps or methods that treat a sample for subsequent amplification and/or detection of Adenovirus nucleic acids present in the sample. The target nucleic acid may be a minority component in the sample. Sample preparation may include any known method of isolating or concentrating components, such as viruses or nucleic acids using standard microbiology methods. Sample preparation may include physical disruption and/or chemical lysis of cellular components to release intracellular components into a substantially aqueous or organic phase and removal of debris, such as by using filtration, centrifugation or adsorption. Sample preparation may include use of a nucleic acid oligonucleotide that selectively or non-specifically captures a target nucleic acid and separates it from other sample components (eg.,as described in U.S. Pat. No. 6,110,678 and PCT Pub. No. WO 2008/016988).

Separating, purifying. These terms mean that one or more components of a sample are removed or separated from other sample components. Sample components include target nucleic acids usually in a generally aqueous solution phase, which may also include cellular fragments, proteins, carbohydrates, lipids, and other nucleic acids. Separating or purifying removes at least 70%, or at least 80%, or at least 95% of the target nucleic acid from other sample components. Ranges of %-purity include all whole and rational numbers of the range.

DNA-dependent DNA polymerase. As used herein, a "DNA-dependent DNA polymerase" is an enzyme that synthesizes a complementary DNA copy from a DNA template. Examples are DNA polymerase I from *E. coli*, bacteriophage T7 DNA polymerase, or DNA polymerases from bacteriophages T4, Phi-29, M2, or T5. DNA-dependent DNA polymerases may be the naturally occurring enzymes isolated from bacteria or bacteriophages or expressed recombinantly, or may be modified or "evolved" forms which have been engineered to possess certain desirable characteristics, e.g., thermostability, or the ability to recognize or synthesize a DNA strand from various modified templates. All known DNA-dependent DNA polymerases require a complementary primer to initiate synthesis. It is known that under suitable conditions a DNA-dependent DNA polymerase may synthesize a complementary DNA copy from an RNA template. RNA-dependent DNA polymerases typically also have DNA-dependent DNA polymerase activity.

DNA-dependent RNA polymerase. As used herein, a "DNA-dependent RNA polymerase" or "transcriptase" is an enzyme that synthesizes multiple RNA copies from a double-stranded or partially double-stranded DNA molecule having a promoter sequence that is usually double-stranded. The RNA molecules ("transcripts") are synthesized in the 5'-to-3' direction beginning at a specific position just downstream of the promoter. Examples of transcriptases are the DNA-dependent RNA polymerase from *E. coli* and bacteriophages T7, T3, and SP6.

RNA-dependent DNA polymerase. As used herein, an "RNA-dependent DNA polymerase" or "reverse transcriptase" ("RT") is an enzyme that synthesizes a complementary DNA copy from an RNA template. All known reverse transcriptases also have the ability to make a complementary DNA copy from a DNA template; thus, they are both RNA- and DNA-dependent DNA polymerases. RTs may also have an RNAse H activity. A primer is required to initiate synthesis with both RNA and DNA templates.

Selective RNAse. As used herein, a "selective RNAse" is an enzyme that degrades the RNA portion of an RNA:DNA duplex but not single-stranded RNA, double-stranded RNA or DNA. An exemplary selective RNAse is RNAse H. Enzymes possessing the same or similar activity as RNAse H may also be used. Selective RNAses may be endonucleases or exonucleases. Most reverse transcriptase enzymes contain an RNAse H activity in addition to their polymerase activities. However, other sources of the RNAse H are available without an associated polymerase activity. The degradation may result in separation of RNA from a RNA:DNA complex. Alternatively, a selective RNAse may simply cut the RNA at various locations such that portions of the RNA melt off or permit enzymes to unwind portions of the RNA. Other enzymes that selectively degrade RNA target sequences or RNA products of the present invention will be readily apparent to those of ordinary skill in the art.

Specificity. The term "specificity," in the context of an amplification system, is used herein to refer to the characteristic of an amplification system which describes its ability to distinguish between target and non-target sequences dependent on sequence and assay conditions. In terms of nucleic acid amplification, specificity generally refers to the ratio of the number of specific amplicons produced to the number of side-products (e.g., the signal-to-noise ratio).

Sensitivity. The term "sensitivity" is used herein to refer to the precision with which a nucleic acid amplification reaction can be detected or quantitated. The sensitivity of an amplification reaction is generally a measure of the smallest copy number of the target nucleic acid that can be reliably detected in the amplification system, and will depend, for example, on the detection assay being employed, and the specificity of the amplification reaction, e.g., the ratio of specific amplicons to side-products.

Relative fluorescence unit. As used herein, the term "relative fluorescence unit" ("RFU") is an arbitrary unit of measurement of fluorescence intensity. RFU varies with the characteristics of the detection means used for the measurement.

Oligonucleotides for the Amplification of Adenovirus

Oligonucleotides for amplifying an Adenovirus target typically comprise at least two amplification oligomers. Some embodiments of the invention may utilise, three, four, five, or even six or ten or more amplification oligomers in, for example, multiplex amplification assays. Thus, by way of example, oligonucleotides for amplifying the Adenovirus target may comprise one, two, three, four, or five or more forward amplification primers and one, two, three, four, or five or more reverse amplification primers. In one embodiment, at least one of the amplification oligomers is configured to specifically hybridize to a region within a target sequence of Adenovirus corresponding to nucleotides 1 to 99 of SEQ ID No. 47. In another embodiment, at least one of the amplification oligomers is configured to specifically hybridize to a region within a target sequence of Adenovirus corresponding to nucleotides 83 to 175 of SEQ ID No. 47. In one embodiment, at least two amplification oligomers are used, wherein each of said at least two amplification oligomers is from 10 to about 50 nucleotides in length and wherein the amplification oligomers are respectively configured to specifically hybridize to regions within a target sequence of Adenovirus selected from the group consisting of from nucleotides 1 to 99 of SEQ ID No. 47 and from nucleotides 83 to 175 of SEQ ID No. 47 in order to generate an amplicon that can be subsequently detected. Suitably the amplicon is detectable using a detection probe. Suitably the amplicon is at least 10, 15, 20, 25, 30, 35, 40, 45, 50, 55, 60, 70 or 80 nucleotides in length.

In one embodiment, at least one of the amplification oligomers is configured to specifically hybridize to a region within a target sequence of Adenovirus corresponding to nucleotides 52 to 99 and/or 40 to 87 and/or 1 to 23 and/or 7 to 23 and/or 7 to 45 of SEQ ID No. 47. In one embodiment, at least one of the amplification oligomers is configured to specifically hybridize to a region within a target sequence of Adenovirus corresponding to nucleotides 139 to 155 and/or 103 to 175 and/or 83 to 99 and/or 83 to 98 of SEQ ID No. 47. In another embodiment, at least two amplification oligomers are used, wherein each of said at least two amplification oligomers is from 10 to about 50 nucleotides in length and wherein the amplification oligomers are respectively configured to specifically hybridize to regions within a target sequence of Adenovirus selected from the group consisting of from nucleotides 52 to 99 and/or 40 to 87 and/or 1 to 23 and/or 7 to 23 and/or 7 to 45 of SEQ ID No. 47 and from nucleotides 139 to 155 and/or 103 to 175 and/or 83 to 99 and/or 83 to 98 of SEQ ID No. 47 in order to generate an amplicon that can be subsequently detected.

In one embodiment, at least one of the amplification oligomers is configured to specifically hybridize to a region within a target sequence of Adenovirus corresponding to nucleotides 52 to 74 and/or 76 to 99 and/or 40 to 56 and/or 65 to 87 and/or 1 to 18 and/or 7 to 23 and/or 28 to 45 and/or 27 to 45 and/or 26 to 45 of SEQ ID No. 47. In one embodiment, at least one of the amplification oligomers is configured to specifically hybridize to a region within a target sequence of Adenovirus corresponding to nucleotides 139 to 155 and/or 103 to 123 and/or 159 to 175 and/or 83 to 99 and/or 83 to 98 of SEQ ID No. 47. In another embodiment, at least two amplification oligomers are used, wherein each of said at least two amplification oligomers is from 10 to about 50 nucleotides in length and wherein the amplification oligomers are respectively configured to specifically hybridize to regions within a target sequence of Adenovirus selected from the group consisting of from nucleotides 52 to 74 and/or 76 to 99 and/or 40 to 56 and/or 65 to 87 and/or 1 to 18 and/or 7 to 23 and/or 28 to 45 and/or 27 to 45 and/or 26 to 45 of SEQ ID No. 47 and from nucleotides 139 to 155 and/or 103 to 123 and/or 159 to 175 and/or 83 to 99 and/or 83 to 98 of SEQ ID No. 47 in order to generate an amplicon that can be subsequently detected.

Oligonucleotides for amplifying and/or detecting the Adenovirus target include oligonucleotide sequences selected from the group consisting of SEQ ID NOS: 1 to 46. Although these sequences are shown as DNA sequences, the sequences include their corresponding RNA sequences, and their complementary (eg. completely complementary) DNA or RNA sequences, including the reverse complements thereof.

Target capture oligomers may include a target-specific sequence that binds specifically to the Adenovirus target nucleic acid and a covalently linked "tail" sequence (eg.

$T_{0-4}A_{10-36}$) used in capturing the hybridization complex containing the target nucleic acid to an immobilized sequence on a solid support. Capture oligomers may include at least one 2' methoxy linkage. Capture oligomers may include the target-specific sequence that binds to Adenovirus nucleic acid attached to another binding moiety, e.g., a biotinylated sequence that binds specifically to immobilized avidin or streptavidin. The tail sequence or binding moiety binds to an immobilized probe (eg., complementary sequence or avidin) to capture the hybridized target and separate it from other sample components by separating the solid support from the mixture.

Primer sequences, including promoter primer sequences, bind specifically to the target nucleic acid or its complementary sequence and may contain additional sequences that are not target-specific, eg., the promoter sequence in a promoter primer. A target-specific sequence, with or without an attached promoter sequence, may serve as an amplification oligomer in a variety of in vitro amplification processes. Embodiments of the Adenovirus assays may use amplification methods that require multiple cycling reaction temperatures, such as PCR (U.S. Pat. Nos. 4,683,195, 4,683,202, and 4,800,159), or may be substantially isothermal as in, for example, transcription associated amplification methods, such as TMA or NASBA (e.g., U.S. Pat. Nos. 5,399,491, 5,480,784, 5,824,518, 5,888,779, 5,786,183, 5,437,990, 5,130,238, 4,868,105, and 5,124,246, and PCT Nos. WO 8801302 and WO 8810315). The Adenovirus assays may use amplification systems that are detected during the amplification process (e.g., real time detection) by including probes that emit distinguishable fluorescent signals when the probe is bound to the intended target sequence made during the amplification process. Probes for real time detection include those referred to as "molecular beacon" or "molecular switch" probes (e.g., U.S. Pat. Nos. 5,118,801 and 5,312,728, Lizardi et al., U.S. Pat. Nos. 5,925,517 and 6,150,097, Tyagi et al., Giesendorf et al., 1998, *Clin. Chem.* 44(3):482-6) and "molecular torch" probes (e.g., U.S. Pat. Nos. 6,835,542 and 6,849,412, Becker et al.). Generally, such probes include a reporter dye attached to one end of the probe oligomer (e.g., FAM™, TET™, JOE™, VIC™) and a quencher compound (e.g., TAMRA™, BHQ1 or non-fluorescent quencher) attached to the other end of the probe oligomer, and signal production depends on whether the two ends with their attached compounds are in close proximity or separated.

The assay to detect Adenovirus in a sample includes the steps of amplifying a target region in the target Adenovirus nucleic acid contained in a sample by using amplification oligomers or primers specific for the intended target region, and detecting the amplified nucleic acid by hybridizing it to a probe sequence. Preferred assays use a PCR or transcription-associated amplification reaction and detection is at the end of the amplification reaction. For detection, the amplified nucleic acid may be labeled and bound to an unlabeled probe, but preferred embodiments bind a labeled probe to the amplified nucleic acid. For real-time detection, a labeled probe may be used that is detected in a homogeneous system.

Embodiments of amplification oligomers specific for Adenovirus nucleic acid include the amplification oligomers comprising, consisting or consisting essentially of a target hybridizing sequence selected from the group consisting of SEQ ID NOS: 1 to 9, 11 to 16, 25 to 28, 31 to 35, 38, and 42 to 46 or a combination of two or more thereof. According to one embodiment, at least one first amplification oligomer comprises, consists of consists essentially of a target hybridizing sequence selected from the group consisting of SEQ ID NOS: 1, 5, 11, 12, 25, 26, 31, 32, 33, 34, 35 or 38 or a combination of two or more thereof. According to one embodiment, at least one second amplification oligomer comprises, consists of consists essentially of a target hybridizing sequence selected from the group consisting of SEQ ID NOS: 2, 3, 6, 7, 8, 9, 13, 14, 15, 16, 27, 28, 42, 43, 44, 45 or 46 or a combination of two or more thereof.

Combinations of amplification oligomers specific for Adenovirus nucleic acid are therefore contemplated.

According to one embodiment, at least one first amplification oligomer comprising, consisting or consisting essentially of a target hybridizing sequence as set forth in SEQ ID NO: 1 is used in combination with at least one second amplification oligomer comprising, consisting or consisting essentially of a target hybridizing sequence as set forth in SEQ ID NO: 2 or SEQ ID NO: 3.

According to another embodiment, at least one first amplification oligomer comprising, consisting or consisting essentially of a target hybridizing sequence as set forth in SEQ ID NO: 5 is used in combination with at least one second amplification oligomer comprising, consisting or consisting essentially of a target hybridizing sequence selected from the group consisting of SEQ ID NO: 6, SEQ ID NO: 7, SEQ ID NO: 8 and SEQ ID NO: 9 or a combination of two or more thereof.

According to another embodiment, at least one first amplification oligomer comprising, consisting or consisting essentially of a target hybridizing sequence as set forth in SEQ ID NO: 11 and/or SEQ ID NO: 12 is used in combination with at least one second amplification oligomer comprising, consisting or consisting essentially of a target hybridizing sequence selected from the group consisting of SEQ ID NO: 13, SEQ ID NO: 14, SEQ ID NO: 15 and SEQ ID NO: 16 or a combination of two or more thereof.

According to another embodiment, at least one first amplification oligomer comprising, consisting or consisting essentially of a target hybridizing sequence as set forth in SEQ ID NO: 25 and/or SEQ ID NO: 26 is used in combination with at least one second amplification oligomer comprising, consisting or consisting essentially of a target hybridizing sequence as set forth in SEQ ID NO: 27 and/or SEQ ID NO: 28. According to one embodiment, at least two first amplification oligomers comprising, consisting or consisting essentially of a target hybridizing sequence as set forth in SEQ ID NO: 25 and SEQ ID NO: 26 are used in combination with at least two second amplification oligomers comprising, consisting or consisting essentially of a target hybridizing sequence as set forth in SEQ ID NO: 27 and SEQ ID NO: 28.

According to another embodiment, at least one first amplification oligomer comprising, consisting or consisting essentially of a target hybridizing sequence selected from the group consisting of SEQ ID NO: 31, SEQ ID NO: 32, SEQ ID NO: 33, SEQ ID NO: 34, SEQ ID NO: 35 and SEQ ID NO: 38 or a combination of two or more thereof is used in combination with at least one second amplification oligomer comprising, consisting or consisting essentially of a target hybridizing sequence as set forth in SEQ ID NO: 27 and/or SEQ ID NO: 28.

According to another embodiment, at least one first amplification oligomer comprising, consisting or consisting essentially of a target hybridizing sequence as set forth in SEQ ID NO: 1 is used in combination with at least one second amplification oligomer comprising, consisting or consisting essentially of a target hybridizing sequence selected from the group consisting of SEQ ID NO:2, SEQ ID NO: 6, SEQ ID NO: 7, SEQ ID NO:8, SEQ ID NO: 9, SEQ ID NO:13, SEQ ID NO:14, SEQ ID NO:15, SEQ ID NO:16, SEQ ID NO:27 or SEQ ID NO:28 or a combination of two or more thereof.

According to another embodiment, at least one first amplification oligomer comprising, consisting or consisting essentially of a target hybridizing sequence as set forth in SEQ ID NO: 5 is used in combination with at least one second amplification oligomer comprising, consisting or consisting essentially of a target hybridizing sequence selected from the group consisting of SEQ ID NO:2, SEQ ID NO: 6, SEQ ID NO: 7, SEQ ID NO:8, SEQ ID NO: 9, SEQ ID NO:13, SEQ ID NO:14, SEQ ID NO:15, SEQ ID NO:16, SEQ ID NO:27 or SEQ ID NO:28 or a combination of two or more thereof.

According to another embodiment, at least one first amplification oligomer comprising, consisting or consisting essentially of a target hybridizing sequence as set forth in SEQ ID NO: 5 is used in combination with at least one second amplification oligomer comprising, consisting or consisting essentially of a target hybridizing sequence selected from the group consisting of SEQ ID NO:2, SEQ ID NO: 6, SEQ ID NO: 7, SEQ ID NO:8, SEQ ID NO: 9, SEQ ID NO:13, SEQ ID NO:14, SEQ ID NO:15, SEQ ID NO:16, SEQ ID NO:27 and SEQ ID NO:28 or a combination of two or more thereof.

According to another embodiment, at least one first amplification oligomer comprising, consisting or consisting essentially of a target hybridizing sequence as set forth in SEQ ID NO: 11 is used in combination with at least one second amplification oligomer comprising, consisting or consisting essentially of a target hybridizing sequence selected from the group consisting of SEQ ID NO:2, SEQ ID NO: 6, SEQ ID NO: 7, SEQ ID NO:8, SEQ ID NO: 9, SEQ ID NO:13, SEQ ID NO:14, SEQ ID NO:15, SEQ ID NO:16, SEQ ID NO:27 and SEQ ID NO:28 or a combination of two or more thereof.

According to another embodiment, at least one first amplification oligomer comprising, consisting or consisting essentially of a target hybridizing sequence as set forth in SEQ ID NO: 12 is used in combination with at least one second amplification oligomer comprising, consisting or consisting essentially of a target hybridizing sequence selected from the group consisting of SEQ ID NO:2, SEQ ID NO: 6, SEQ ID NO: 7, SEQ ID NO:8, SEQ ID NO: 9, SEQ ID NO:13, SEQ ID NO:14, SEQ ID NO:15, SEQ ID NO:16, SEQ ID NO:27 and SEQ ID NO:28 or a combination of two or more thereof.

According to another embodiment, at least one first amplification oligomer comprising, consisting or consisting essentially of a target hybridizing sequence as set forth in SEQ ID NO: 25 is used in combination with at least one second amplification oligomer comprising, consisting or consisting essentially of a target hybridizing sequence selected from the group consisting of SEQ ID NO:2, SEQ ID NO: 6, SEQ ID NO: 7, SEQ ID NO:8, SEQ ID NO: 9, SEQ ID NO:13, SEQ ID NO:14, SEQ ID NO:15, SEQ ID NO:16, SEQ ID NO:27 and SEQ ID NO:28 or a combination of two or more thereof.

According to another embodiment, at least one first amplification oligomer comprising, consisting or consisting essentially of a target hybridizing sequence as set forth in SEQ ID NO: 26 is used in combination with at least one second amplification oligomer comprising, consisting or consisting essentially of a target hybridizing sequence selected from the group consisting of SEQ ID NO:2, SEQ ID NO: 6, SEQ ID NO: 7, SEQ ID NO:8, SEQ ID NO: 9, SEQ ID NO:13, SEQ ID NO:14, SEQ ID NO:15, SEQ ID NO:16, SEQ ID NO:27 and SEQ ID NO:28 or a combination of two or more thereof.

According to another embodiment, at least one first amplification oligomer comprising, consisting or consisting essentially of a target hybridizing sequence as set forth in SEQ ID NO: 31 is used in combination with at least one second amplification oligomer comprising, consisting or consisting essentially of a target hybridizing sequence selected from the group consisting of SEQ ID NO:2, SEQ ID NO: 6, SEQ ID NO: 7, SEQ ID NO:8, SEQ ID NO: 9, SEQ ID NO:13, SEQ ID NO:14, SEQ ID NO:15, SEQ ID NO:16, SEQ ID NO:27 and SEQ ID NO:28 or a combination of two or more thereof.

According to another embodiment, at least one first amplification oligomer comprising, consisting or consisting essentially of a target hybridizing sequence as set forth in SEQ ID NO: 32 is used in combination with at least one second amplification oligomer comprising, consisting or consisting essentially of a target hybridizing sequence selected from the group consisting of SEQ ID NO:2, SEQ ID NO: 6, SEQ ID NO: 7, SEQ ID NO:8, SEQ ID NO: 9, SEQ ID NO:13, SEQ ID NO:14, SEQ ID NO:15, SEQ ID NO:16, SEQ ID NO:27 and SEQ ID NO:28 or a combination of two or more thereof.

According to another embodiment, at least one first amplification oligomer comprising, consisting or consisting essentially of a target hybridizing sequence selected from the group consisting of SEQ ID NO: 1, SEQ ID NO: 5, SEQ ID NO:11, SEQ ID NO:12, SEQ ID NO:25, SEQ ID NO:26, SEQ ID NO:31, SEQ ID NO:32, SEQ ID NO:33, SEQ ID NO:34, SEQ ID NO:35 and SEQ ID NO:38 or a combination of two or more thereof is used in combination with at least one second amplification oligomer comprising, consisting or consisting essentially of a target hybridizing sequence as set forth in SEQ ID NO:2.

According to another embodiment, at least one first amplification oligomer comprising, consisting or consisting essentially of a target hybridizing sequence selected from the group consisting of SEQ ID NO: 1, SEQ ID NO: 5, SEQ ID NO:11, SEQ ID NO:12, SEQ ID NO:25, SEQ ID NO:26, SEQ ID NO:31, SEQ ID NO:32, SEQ ID NO:33, SEQ ID NO:34, SEQ ID NO:35 and SEQ ID NO:38 or a combination of two or more thereof is used in combination with at least one second amplification oligomer comprising, consisting or consisting essentially of a target hybridizing sequence as set forth in SEQ ID NO:3.

According to another embodiment, at least one first amplification oligomer comprising, consisting or consisting essentially of a target hybridizing sequence selected from the group consisting of SEQ ID NO: 1, SEQ ID NO: 5, SEQ ID NO:11, SEQ ID NO:12, SEQ ID NO:25, SEQ ID NO:26, SEQ ID NO:31, SEQ ID NO:32, SEQ ID NO:33, SEQ ID NO:34, SEQ ID NO:35 and SEQ ID NO:38 or a combination of two or more thereof is used in combination with at least one second amplification oligomer comprising, consisting or consisting essentially of a target hybridizing sequence as set forth in SEQ ID NO:6.

According to another embodiment, at least one first amplification oligomer comprising, consisting or consisting essentially of a target hybridizing sequence selected from the group consisting of SEQ ID NO: 1, SEQ ID NO: 5, SEQ ID NO:11, SEQ ID NO:12, SEQ ID NO:25, SEQ ID NO:26, SEQ ID NO:31, SEQ ID NO:32, SEQ ID NO:33, SEQ ID NO:34, SEQ ID NO:35 and SEQ ID NO:38 or a combination of two or more thereof is used in combination with at least one second amplification oligomer comprising, consisting or consisting essentially of a target hybridizing sequence as set forth in SEQ ID NO:7.

According to another embodiment, at least one first amplification oligomer comprising, consisting or consisting essentially of a target hybridizing sequence selected from the group consisting of SEQ ID NO: 1, SEQ ID NO: 5, SEQ ID NO:11, SEQ ID NO:12, SEQ ID NO:25, SEQ ID NO:26, SEQ ID NO:31, SEQ ID NO:32, SEQ ID NO:33, SEQ ID NO:34, SEQ ID NO:35 and SEQ ID NO:38 or a combination of two or more thereof is used in combination with at least one second amplification oligomer comprising, consisting or consisting essentially of a target hybridizing sequence as set forth in SEQ ID NO:8.

According to another embodiment, at least one first amplification oligomer comprising, consisting or consisting essentially of a target hybridizing sequence selected from the group consisting of SEQ ID NO: 1, SEQ ID NO: 5, SEQ ID NO:11, SEQ ID NO:12, SEQ ID NO:25, SEQ ID NO:26, SEQ ID NO:31, SEQ ID NO:32, SEQ ID NO:33, SEQ ID NO:34, SEQ ID NO:35 and SEQ ID NO:38 or a combination of two or more thereof is used in combination with at least one second amplification oligomer comprising, consisting or consisting essentially of a target hybridizing sequence as set forth in SEQ ID NO:9.

According to another embodiment, at least one first amplification oligomer comprising, consisting or consisting essentially of a target hybridizing sequence selected from the group consisting of SEQ ID NO: 1, SEQ ID NO: 5, SEQ ID NO:11, SEQ ID NO:12, SEQ ID NO:25, SEQ ID NO:26, SEQ ID NO:31, SEQ ID NO:32, SEQ ID NO:33, SEQ ID NO:34, SEQ ID NO:35 and SEQ ID NO:38 or a combination of two or more thereof is used in combination with at least one second amplification oligomer comprising, consisting or consisting essentially of a target hybridizing sequence as set forth in SEQ ID NO:13.

According to another embodiment, at least one first amplification oligomer comprising, consisting or consisting essentially of a target hybridizing sequence selected from the group consisting of SEQ ID NO: 1, SEQ ID NO: 5, SEQ ID NO:11, SEQ ID NO:12, SEQ ID NO:25, SEQ ID NO:26, SEQ ID NO:31, SEQ ID NO:32, SEQ ID NO:33, SEQ ID NO:34, SEQ ID NO:35 and SEQ ID NO:38 or a combination of two or more thereof is used in combination with at least one second amplification oligomer comprising, consisting or consisting essentially of a target hybridizing sequence as set forth in SEQ ID NO:14.

According to another embodiment, at least one first amplification oligomer comprising, consisting or consisting essentially of a target hybridizing sequence selected from the group consisting of SEQ ID NO: 1, SEQ ID NO: 5, SEQ ID NO:11, SEQ ID NO:12, SEQ ID NO:25, SEQ ID NO:26, SEQ ID NO:31, SEQ ID NO:32, SEQ ID NO:33, SEQ ID NO:34, SEQ ID NO:35 and SEQ ID NO:38 or a combination of two or more thereof is used in combination with at least one second amplification oligomer comprising, consisting or consisting essentially of a target hybridizing sequence as set forth in SEQ ID NO:15.

According to another embodiment, at least one first amplification oligomer comprising, consisting or consisting essentially of a target hybridizing sequence selected from the group consisting of SEQ ID NO: 1, SEQ ID NO: 5, SEQ ID NO:11 SEQ ID NO:12, SEQ ID NO:25, SEQ ID NO:26, SEQ ID NO:31, SEQ ID NO:32, SEQ ID NO:33, SEQ ID NO:34, SEQ ID NO:35 and SEQ ID NO:38 or a combination of two or more thereof is used in combination with at least one second amplification oligomer comprising, con-sisting or consisting essentially of a target hybridizing sequence as set forth in SEQ ID NO:16.

According to another embodiment, at least one first amplification oligomer comprising, consisting or consisting essentially of a target hybridizing sequence selected from the group consisting of SEQ ID NO: 1, SEQ ID NO: 5, SEQ ID NO:11, SEQ ID NO:12, SEQ ID NO:25, SEQ ID NO:26, SEQ ID NO:31, SEQ ID NO:32, SEQ ID NO:33, SEQ ID NO:34, SEQ ID NO:35 and SEQ ID NO:38 or a combination of two or more thereof is used in combination with at least one second amplification oligomer comprising, consisting or consisting essentially of a target hybridizing sequence as set forth in SEQ ID NO:27.

According to another embodiment, at least one first amplification oligomer comprising, consisting or consisting essentially of a target hybridizing sequence selected from the group consisting of SEQ ID NO: 1, SEQ ID NO: 5, SEQ ID NO:11, SEQ ID NO:12, SEQ ID NO:25, SEQ ID NO:26, SEQ ID NO:31, SEQ ID NO:32, SEQ ID NO:33, SEQ ID NO:34, SEQ ID NO:35 and SEQ ID NO:38 or a combination of two or more thereof is used in combination with at least one second amplification oligomer comprising, consisting or consisting essentially of a target hybridizing sequence as set forth in SEQ ID NO:28.

The methods for detecting Adenovirus nucleic acid optionally include a detecting step that uses at least one probe that binds specifically to the amplified Adenovirus product (RNA or DNA amplicon, preferably DNA amplicon). Preferably, the probe is labeled and produces a signal detected in a homogeneous system, that is, without separation of bound probe from unbound probe. Other examples of probes may be labeled with a fluorescent compound which emits a detectable signal only when the probe is bound to its target, e.g., molecular switch, beacon, Taqman or torch probes as further described herein.

Probes comprise polynucleotides or polynucleotide analogs and optionally may carry a detectable label covalently bonded thereto. Nucleosides or nucleoside analogs of the probe may comprise nitrogenous heterocyclic bases, or base analogs, where the nucleosides are linked together, for example by phospohdiester bonds to form a polynucleotide. Accordingly, a probe may comprise conventional ribonucleic acid (RNA) and/or deoxyribonucleic acid (DNA), but also may comprise chemical analogs of these molecules. The "backbone" of a probe may be made up of a variety of linkages known in the art, including one or more sugar-phosphodiester linkages, peptide-nucleic acid bonds (sometimes referred to as "peptide nucleic acids" as described by Hyldig-Nielsen et al., PCT Intl Pub. No. WO 95/32305), phosphorothioate linkages, methylphosphonate linkages or combinations thereof. Sugar moieties of the probe may be either ribose or deoxyribose, or similar compounds having known substitutions, such as, for example, 2'-O-methyl ribose and 2' halide substitutions (e.g., 2'-F). The nitrogenous bases may be conventional bases (A, G, C, T, U), known analogs thereof (e.g., inosine or "I"; see The Biochemistry of the Nucleic Acids 5-36, Adams et al., ed., 11th ed., 1992), known derivatives of purine or pyrimidine bases (e.g., $N^4$-methyl deoxygaunosine, deaza- or aza-purines and deaza- or aza-pyrimidines, pyrimidine bases having substituent groups at the 5 or 6 position, purine bases having an altered or a replacement substituent at the 2, 6 or 8 positions, 2-amino-6-methylaminopurine, $O^6$-methylguanine, 4-thio-pyrimidines, 4-amino-pyrimidines, 4-dimethylhydrazine-pyrimidines, and $O^4$-alkyl-pyrimidines (see, Cook, PCT Int'l Pub. No. WO 93/13121) and "abasic" residues where the backbone includes no nitrogenous base for one or more residues of the polymer (see Arnold et al., U.S. Pat. No. 5,585,481). A probe may comprise only conventional sugars, bases and linkages found in RNA and DNA, or may include both conventional components and substitutions (e.g., conventional bases linked via a methoxy backbone, or a nucleic acid including conventional bases and one or more base analogs). While oligonucleotide probes of different lengths and base composition may be used for detecting Adenovirus nucleic acids, preferred probes in this invention have lengths of up to 100 nucleotides, and more preferably have lengths of up to 60 nucleotides. Preferred length ranges for the invented oligonucleotides are from 10 to 100 bases in length, or more preferably between 15 and 50 bases in length, or still more preferably between 15 and 40 bases in length, or still more preferably between 15 and 30 bases in length. However, the specific probe sequences described herein also may be provided in a nucleic acid cloning vector or transcript or other longer nucleic acid and still can be used for detecting Adenovirus nucleic acids.

In one embodiment, one or more detection probes are configured to detect a sequence in a region corresponding to nucleotides 74 to 139 of SEQ ID NO:47; and/or nucleotides 56 to 103 of SEQ ID NO:47; and/or nucleotides 18 to 83 of SEQ ID NO:47; and/or nucleotides 23 to 83 of SEQ ID NO:47; and/or nucleotides 23 to 83 of SEQ ID NO:47; and/or nucleotides 23 to 83 of SEQ ID NO:47 and/or nucleotides 52 to 99 of SEQ ID NO:47.

In another embodiment, one or more of the detection probes are configured to target a sequence in a region corresponding to nucleotides 76 to 99 and/or nucleotides 65 to 87 and/or nucleotides 53 to 76 and/or nucleotides 53 and/or 74 or nucleotides 53 and/or 72 or nucleotides 52 to 71.

Probes for the specific detection of Adenovirus sequences include oligomers selected from the group consisting of SEQ ID Nos. 4, 10, 17, 18, 19, 20, 21, 22, 23, 24, 29, 30, 36, 37, 39 and 40 or a combination of two or more thereof.

Although these sequences are shown as DNA sequences, the sequences include their corresponding RNA sequences, and their complementary (eg. completely complementary) DNA or RNA sequences, including the reverse complements thereof.

Assays for detection of Adenovirus nucleic acid may include an internal control (IC) nucleic acid that is amplified and detected by using IC-specific primers and probe in the same reaction mixtures used for Adenovirus nucleic acid amplification and detection. Amplification and detection of the IC-specific sequence demonstrates that assay reagents and conditions were properly used even when no Adenovirus-specific signal is detected for a tested sample (i.e., negative samples). The IC may be used as an internal calibrator for the assay that provides a quantitative result. The IC may be a randomized sequence derived from a naturally occurring source that is not Adenovirus.

Combinations and Compositions of Oligonucleotides for the Amplification and Detection of Adenovirus Combinations of oligomers and probes that can be used for the amplification and detection of Adenovirus are also disclosed.

Oligonucleotides for amplifying and detecting the Adenovirus target typically comprise at least two amplification oligomers and at least one probe. Some embodiments of the invention may utilise, three, four, five, or even six or more amplification oligomers and two, three, four, five or even six or more probes. Thus, by way of example, oligonucleotides for amplifying and detecting the Adenovirus target may comprise one, two or three or more forward amplification primers together with one, two or three or more reverse amplification primers together with one, two, three, four, five or even six or more probes.

In one embodiment, at least one of the amplification oligomers is configured to specifically hybridize to a region within a target sequence of Adenovirus corresponding to nucleotides 1 to 99 of SEQ ID No. 47 and a probe is configured to detect a sequence in a region corresponding to nucleotides 52 to 99 of SEQ ID NO:47.

In another embodiment, at least one of the amplification oligomers is configured to specifically hybridize to a region within a target sequence of Adenovirus corresponding to nucleotides 83 to 175 of SEQ ID No. 47 and a probe is configured to detect a sequence in a region corresponding to nucleotides 52 to 99 of SEQ ID NO:47.

In one embodiment, at least two amplification oligomers are used, wherein each of said at least two amplification oligomers is from 10 to about 50 nucleotides in length and wherein the amplification oligomers are respectively configured to specifically hybridize to regions within a target sequence of Adenovirus selected from the group consisting of from nucleotides 1 to 99 of SEQ ID No. 47 and from nucleotides 83 to 175 of SEQ ID No. 47 and a probe is configured to detect a sequence in a region corresponding to nucleotides 52 to 99 of SEQ ID NO:47.

In one embodiment, at least one of the amplification oligomers is configured to specifically hybridize to a region within a target sequence of Adenovirus corresponding to nucleotides 52 to 99 and/or 40 to 87 and/or 1 to 23 and/or 7 to 23 and/or 7 to 45 of SEQ ID No. 47 and a probe is configured to detect a sequence in a region corresponding to nucleotides 52 to 99 of SEQ ID NO:47—such as nucleotides 76 to 99 or nucleotides 65 to 87 or nucleotides 53 to 76 or nucleotides 53 to 74 or nucleotides 53 to 72 or nucleotides 52 to 71.

In one embodiment, at least one of the amplification oligomers is configured to specifically hybridize to a region within a target sequence of Adenovirus corresponding to nucleotides 139 to 155 and/or 103 to 175 and/or 83 to 99 and/or 83 to 98 of SEQ ID No. 47 and a probe is configured to detect a sequence in a region corresponding to nucleotides 52 to 99 of SEQ ID NO:47—such as nucleotides 76 to 99 or nucleotides 65 to 87 or nucleotides 53 to 76 or nucleotides 53 to 74 or nucleotides 53 to 72 or nucleotides 52 to 71.

In another embodiment, at least two amplification oligomers are used, wherein each of said at least two amplification oligomers is from 10 to about 50 nucleotides in length and wherein the amplification oligomers are respectively configured to specifically hybridize to regions within a target sequence of Adenovirus selected from the group consisting of from nucleotides 52 to 99 and/or 40 to 87 and/or 1 to 23 and/or 7 to 23 and/or 7 to 45 of SEQ ID No. 47 and from nucleotides 139 to 155 and/or 103 to 175 and/or 83 to 99 and/or 83 to 98 of SEQ ID No. 47 and a probe is configured to detect a sequence in a region corresponding to nucleotides 52 to 99 of SEQ ID NO:47—such as nucleotides 76 to 99 or nucleotides 65 to 87 or nucleotides 53 to 76 or nucleotides 53 to 74 or nucleotides 53 to 72 or nucleotides 52 to 71.

In one embodiment, at least one of the amplification oligomers is configured to specifically hybridize to a region within a target sequence of Adenovirus corresponding to nucleotides 52 to 74 and/or 76 to 99 and/or 40 to 56 and/or 65 to 87 and/or 1 to 18 and/or 7 to 23 and/or 28 to 45 and/or 27 to 45 and/or 26 to 45 of SEQ ID No. 47 and a probe is configured to detect a sequence in a region corresponding to nucleotides 52 to 99 of SEQ ID NO:47—such as nucleotides 76 to 99 or nucleotides 65 to 87 or nucleotides 53 to 76 or nucleotides 53 to 74 or nucleotides 53 to 72 or nucleotides 52 to 71.

In another embodiment, at least one of the amplification oligomers is configured to specifically hybridize to a region within a target sequence of Adenovirus corresponding to nucleotides 139 to 155 and/or 103 to 123 and/or 159 to 175 and/or 83 to 99 and/or 83 to 98 of SEQ ID No. 47 and a probe is configured to detect a sequence in a region corresponding to nucleotides 52 to 99 of SEQ ID NO:47—such as nucleotides 76 to 99 or nucleotides 65 to 87 or nucleotides 53 to 76 or nucleotides 53 to 74 or nucleotides 53 to 72 or nucleotides 52 to 71.

In another embodiment, at least two amplification oligomers are used, wherein each of said at least two amplification oligomers is from 10 to about 50 nucleotides in length and wherein the amplification oligomers are respectively configured to specifically hybridize to regions within a target sequence of Adenovirus selected from the group consisting of from nucleotides 52 to 74 and/or 76 to 99 and/or 40 to 56 and/or 65 to 87 and/or 1 to 18 and/or 7 to 23 and/or 28 to 45 and/or 27 to 45 and/or 26 to 45 of SEQ ID No. 47 and from nucleotides 139 to 155 and/or 103 to 123 and/or 159 to 175 and/or 83 to 99 and/or 83 to 98 of SEQ ID No. 47 and a probe is configured to detect a sequence in a region corresponding to nucleotides 52 to 99 of SEQ ID NO:47—such as nucleotides 76 to 99 or nucleotides 65 to 87 or nucleotides 53 to 76 or nucleotides 53 to 74 or nucleotides 53 to 72 or nucleotides 52 to 71.

According to one embodiment, a first amplification oligomer comprising, consisting or consisting essentially of a target hybridizing sequence as set forth in SEQ ID NO: 1 is used in combination with a second amplification oligomer comprising, consisting or consisting essentially of a target hybridizing sequence as set forth in SEQ ID NO: 2 and/or SEQ ID NO: 3 together with a probe comprising, consisting or consisting essentially of a sequence selected from the group consisting of SEQ ID Nos. 4, 10, 17, 18, 19, 20, 21, 22, 23, 24, 29, 30, 36, 37, 39 and 40 or a combination of two or more thereof, preferably, SEQ ID No. 4.

According to another embodiment, a first amplification oligomer comprising, consisting or consisting essentially of a target hybridizing sequence as set forth in SEQ ID NO: 5 is used in combination with at least one second amplification oligomer comprising, consisting or consisting essentially of a target hybridizing sequence as set forth in SEQ ID NO: 6 and/or SEQ ID NO: 7 and/or SEQ ID NO: 8 and/or SEQ ID NO: 9 together with a probe comprising, consisting or consisting essentially of a sequence selected from the group consisting of SEQ ID Nos. 4, 10, 17, 18, 19, 20, 21, 22, 23, 24, 29, 30, 36, 37, 39 and 40 or a combination of two or more thereof, preferably, SEQ ID No. 10.

According to another embodiment, at least one first amplification oligomer comprising, consisting or consisting essentially of a target hybridizing sequence as set forth in SEQ ID NO: 11 and/or SEQ ID NO: 12 is used in combination with at least one second amplification oligomer comprising, consisting or consisting essentially of a target hybridizing sequence as set forth in SEQ ID NO: 13 and/or SEQ ID NO: 14 and/or SEQ ID NO: 15 and/or SEQ ID NO: 16 together with a probe comprising, consisting or consisting essentially of a sequence selected from the group consisting of SEQ ID Nos. 4, 10, 17, 18, 19, 20, 21, 22, 23, 24, 29, 30, 36, 37, 39 and 40 or a combination of two or more thereof, preferably, a probe comprising, consisting or consisting essentially of a sequence selected from the group consisting of SEQ ID Nos 17 to 24 or a combination of two or more thereof.

According to another embodiment, at least one first amplification oligomer comprising, consisting or consisting essentially of a target hybridizing sequence as set forth in SEQ ID NO: 25 and/or SEQ ID NO: 26 is used in combination with at least one second amplification oligomer comprising, consisting or consisting essentially of a target hybridizing sequence as set forth in SEQ ID NO: 27 and/or SEQ ID NO: 28 together with a probe comprising, consisting or consisting essentially of a sequence selected from the group consisting of SEQ ID Nos. 4, 10, 17, 18, 19, 20, 21, 22, 23, 24, 29, 30, 36, 37, 39 and 40 or a combination of two or more thereof, preferably, SEQ ID Nos 29 and/or 30.

According to another embodiment, at least one first amplification oligomer comprising, consisting or consisting essentially of a target hybridizing sequence as set forth in SEQ ID NO: 31 and/or SEQ ID NO: 32 and/or SEQ ID NO: 33 and/or SEQ ID NO: 34 and/or SEQ ID NO: 35 and/or SEQ ID NO: 38 is used in combination with at least one second amplification oligomer comprising, consisting or consisting essentially of a target hybridizing sequence as set forth in SEQ ID NO: 27 and/or SEQ ID NO: 28 together with a probe comprising, consisting or consisting essentially of a sequence selected from the group consisting of SEQ ID Nos. 4, 10, 17, 18, 19, 20, 21, 22, 23, 24, 29, 30, 36, 37, 39 and 40 or a combination of two or more thereof, preferably, a probe comprising, consisting or consisting essentially of a sequence selected from the group consisting of SEQ ID Nos 36, 37, 39 and 40 or a combination of two or more thereof.

According to another embodiment, a first amplification oligomer comprising, consisting or consisting essentially of a target hybridizing sequence as set forth in SEQ ID NO: 1 is used in combination with at least one second amplification oligomer comprising, consisting or consisting essentially of a target hybridizing sequence as set forth in SEQ ID NO:2, SEQ ID NO: 6, SEQ ID NO: 7, SEQ ID NO:8, SEQ ID NO: 9, SEQ ID NO:13, SEQ ID NO:14, SEQ ID NO:15, SEQ ID NO:16, SEQ ID NO:27 and SEQ ID NO:28 or a combination of two or more thereof together with a probe comprising, consisting or consisting essentially of a sequence selected from the group consisting of SEQ ID Nos. 4, 10, 17, 18, 19, 20, 21, 22, 23, 24, 29, 30, 36, 37, 39 and 40 or a combination of two or more thereof, preferably, SEQ ID No. 4.

According to another embodiment, a first amplification oligomer comprising, consisting or consisting essentially of a target hybridizing sequence as set forth in SEQ ID NO: 5 is used in combination with at least one second amplification oligomer comprising, consisting or consisting essentially of a target hybridizing sequence selected from the group consisting of SEQ ID NO:2, SEQ ID NO: 6, SEQ ID NO: 7, SEQ ID NO:8, SEQ ID NO: 9, SEQ ID NO:13, SEQ ID NO:14, SEQ ID NO:15, SEQ ID NO:16, SEQ ID NO:27 and SEQ ID NO:28 or a combination of two or more thereof together with a probe comprising, consisting or consisting essentially of a sequence selected from the group consisting of SEQ ID Nos. 4, 10, 17, 18, 19, 20, 21, 22, 23, 24, 29, 30, 36, 37, 39 and 40 or a combination of two or more thereof, preferably, SEQ ID No. 10.

According to another embodiment, a first amplification oligomer comprising, consisting or consisting essentially of a target hybridizing sequence as set forth in SEQ ID NO: 11 is used in combination with at least one second amplification oligomer comprising, consisting or consisting essentially of a target hybridizing sequence selected from the group consisting of SEQ ID NO:2, SEQ ID NO: 6, SEQ ID NO: 7, SEQ ID NO:8, SEQ ID NO: 9, SEQ ID NO:13, SEQ ID NO:14, SEQ ID NO:15, SEQ ID NO:16, SEQ ID NO:27 and SEQ ID NO:28 or a combination of two or more thereof together with a probe comprising, consisting or consisting essentially of a sequence selected from the group consisting of SEQ ID Nos. 4, 10, 17, 18, 19, 20, 21, 22, 23, 24, 29, 30, 36, 37, 39 and 40 or a combination of two or more thereof, preferably, a probe comprising, consisting or consisting essentially of a sequence selected from the group consisting of SEQ ID Nos 17 to 24 or a combination of two or more thereof.

According to another embodiment, a first amplification oligomer comprising, consisting or consisting essentially of a target hybridizing sequence as set forth in SEQ ID NO: 12 is used in combination with at least one second amplification oligomer comprising, consisting or consisting essentially of a target hybridizing sequence selected from the group consisting of SEQ ID NO:2, SEQ ID NO: 6, SEQ ID NO: 7, SEQ ID NO:8, SEQ ID NO: 9, SEQ ID NO:13, SEQ ID NO:14, SEQ ID NO:15, SEQ ID NO:16, SEQ ID NO:27 and SEQ ID NO:28 or a combination of two or more thereof together with a probe comprising, consisting or consisting essentially of a sequence selected from the group consisting of SEQ ID Nos. 4, 10, 17, 18, 19, 20, 21, 22, 23, 24, 29, 30, 36, 37, 39 and 40 or a combination of two or more thereof, preferably, a probe comprising, consisting or consisting essentially of a sequence selected from the group consisting of SEQ ID Nos 17 to 24 or a combination of two or more thereof.

According to another embodiment, a first amplification oligomer comprising, consisting or consisting essentially of a target hybridizing sequence as set forth in SEQ ID NO: 25 is used in combination with at least one second amplification oligomer comprising, consisting or consisting essentially of a target hybridizing sequence selected from the group consisting of SEQ ID NO:2, SEQ ID NO: 6, SEQ ID NO: 7, SEQ ID NO:8, SEQ ID NO: 9, SEQ ID NO:13, SEQ ID NO:14, SEQ ID NO:15, SEQ ID NO:16, SEQ ID NO:27 and SEQ ID NO:28 or a combination of two or more thereof together with a probe comprising, consisting or consisting essentially of a sequence selected from the group consisting of SEQ ID Nos. 4, 10, 17, 18, 19, 20, 21, 22, 23, 24, 29, 30, 36, 37, 39 and 40 or a combination of two or more thereof, preferably, a probe comprising, consisting or consisting essentially of a sequence selected from the group consisting of SEQ ID Nos 29 and 30 or a combination of two or more thereof.

According to another embodiment, a first amplification oligomer comprising, consisting or consisting essentially of a target hybridizing sequence as set forth in SEQ ID NO: 26 is used in combination with at least one second amplification oligomer comprising, consisting or consisting essentially of a target hybridizing sequence selected from the group consisting of SEQ ID NO:2, SEQ ID NO: 6, SEQ ID NO: 7, SEQ ID NO:8, SEQ ID NO: 9, SEQ ID NO:13, SEQ ID NO:14, SEQ ID NO:15, SEQ ID NO:16, SEQ ID NO:27 and SEQ ID NO:28 or a combination of two or more thereof together with a probe comprising, consisting or consisting essentially of a sequence selected from the group consisting of SEQ ID Nos. 4, 10, 17, 18, 19, 20, 21, 22, 23, 24, 29, 30, 36, 37, 39 and 40 or a combination of two or more thereof, preferably, a probe comprising, consisting or consisting essentially of a sequence selected from the group consisting of SEQ ID Nos 29 and 30 or a combination thereof.

According to another embodiment, a first amplification oligomer comprising, consisting or consisting essentially of a target hybridizing sequence as set forth in SEQ ID NO: 31 is used in combination with at least one second amplification oligomer comprising, consisting or consisting essentially of a target hybridizing sequence selected from the group consisting of SEQ ID NO:2, SEQ ID NO: 6, SEQ ID NO: 7, SEQ ID NO:8, SEQ ID NO: 9, SEQ ID NO:13, SEQ ID NO:14, SEQ ID NO:15, SEQ ID NO:16, SEQ ID NO:27 and SEQ ID NO:28 or a combination of two or more thereof together with a probe comprising, consisting or consisting essentially of a sequence selected from the group consisting of SEQ ID Nos. 4, 10, 17, 18, 19, 20, 21, 22, 23, 24, 29, 30, 36, 37, 39 and 40 or a combination of two or more thereof, preferably, a probe comprising, consisting or consisting essentially of a sequence selected from the group consisting of SEQ ID Nos 36, 37, 39 and 40 or a combination of two or more thereof.

According to another embodiment, a first amplification oligomer comprising, consisting or consisting essentially of a target hybridizing sequence as set forth in SEQ ID NO: 32 is used in combination with at least one second amplification oligomer comprising, consisting or consisting essentially of a target hybridizing sequence selected from the group consisting of SEQ ID NO:2, SEQ ID NO: 6, SEQ ID NO: 7, SEQ ID NO:8, SEQ ID NO: 9, SEQ ID NO:13, SEQ ID NO:14, SEQ ID NO:15, SEQ ID NO:16, SEQ ID NO:27 and SEQ ID NO:28 or a combination of two or more thereof together with a probe comprising, consisting or consisting essentially of a sequence selected from the group consisting of SEQ ID Nos. 4, 10, 17, 18, 19, 20, 21, 22, 23, 24, 29, 30, 36, 37, 39 and 40 or a combination of two or more thereof, preferably, a probe comprising, consisting or consisting essentially of a sequence selected from the group consisting of SEQ ID Nos 36, 37, 39 and 40 or a combination of two or more thereof.

According to another embodiment, a first amplification oligomer comprising, consisting or consisting essentially of a target hybridizing sequence as set forth in SEQ ID NO: 33 is used in combination with at least one second amplification oligomer comprising, consisting or consisting essentially of a target hybridizing sequence selected from the group consisting of SEQ ID NO:2, SEQ ID NO: 6, SEQ ID NO: 7, SEQ ID NO:8, SEQ ID NO: 9, SEQ ID NO:13, SEQ ID NO:14, SEQ ID NO:15, SEQ ID NO:16, SEQ ID NO:27 and SEQ ID NO:28 or a combination of two or more thereof together with a probe comprising, consisting or consisting essentially of a sequence selected from the group consisting of SEQ ID Nos. 4, 10, 17, 18, 19, 20, 21, 22, 23, 24, 29, 30, 36, 37, 39 and 40 or a combination of two or more thereof, preferably, a probe comprising, consisting or consisting essentially of a sequence selected from the group consisting of SEQ ID Nos 36, 37, 39 and 40 or a combination of two or more thereof.

According to another embodiment, a first amplification oligomer comprising, consisting or consisting essentially of a target hybridizing sequence selected from the group consisting of SEQ ID NO: 1, SEQ ID NO: 5, SEQ ID NO:11, SEQ ID NO:12, SEQ ID NO:25, SEQ ID NO:26, SEQ ID NO:31, SEQ ID NO:32, SEQ ID NO:33, SEQ ID NO:34, SEQ ID NO:35 and SEQ ID NO:38 or a combination of two or more thereof is used in combination with a second amplification oligomer comprising, consisting or consisting essentially of a target hybridizing sequence as set forth in SEQ ID NO:2 together with a probe comprising, consisting or consisting essentially of a sequence selected from the group consisting of SEQ ID Nos. 4, 10, 17, 18, 19, 20, 21, 22, 23, 24, 29, 30, 36, 37, 39 and 40 or a combination of two or more thereof, preferably, SEQ ID No. 4.

According to another embodiment, a first amplification oligomer comprising, consisting or consisting essentially of a target hybridizing sequence selected from the group consisting of SEQ ID NO: 1, SEQ ID NO: 5, SEQ ID NO:11, SEQ ID NO:12, SEQ ID NO:25, SEQ ID NO:26, SEQ ID NO:31, SEQ ID NO:32, SEQ ID NO:33, SEQ ID NO:34, SEQ ID NO:35 and SEQ ID NO:38 or a combination of two or more thereof is used in combination with a second amplification oligomer comprising, consisting or consisting essentially of a target hybridizing sequence as set forth in SEQ ID NO:3 together with a probe comprising, consisting or consisting essentially of a sequence selected from the group consisting of SEQ ID Nos. 4, 10, 17, 18, 19, 20, 21, 22, 23, 24, 29, 30, 36, 37, 39 and 40 or a combination of two or more thereof, preferably, SEQ ID No. 4.

According to another embodiment, a first amplification oligomer comprising, consisting or consisting essentially of a target hybridizing sequence selected from the group consisting of SEQ ID NO: 1, SEQ ID NO: 5, SEQ ID NO:11, SEQ ID NO:12, SEQ ID NO:25, SEQ ID NO:26, SEQ ID NO:31, SEQ ID NO:32, SEQ ID NO:33, SEQ ID NO:34, SEQ ID NO:35 and SEQ ID NO:38 or a combination of two or more thereof is used in combination with a second amplification oligomer comprising, consisting or consisting essentially of a target hybridizing sequence as set forth in SEQ ID NO:6 together with a probe comprising, consisting or consisting essentially of a sequence selected from the group consisting of SEQ ID Nos. 4, 10, 17, 18, 19, 20, 21, 22, 23, 24, 29, 30, 36, 37, 39 and 40 or a combination of two or more thereof, preferably, SEQ ID No. 4.

According to another embodiment, a first amplification oligomer comprising, consisting or consisting essentially of a target hybridizing sequence selected from the group consisting of SEQ ID NO: 1, SEQ ID NO: 5, SEQ ID NO:11, SEQ ID NO:12, SEQ ID NO:25, SEQ ID NO:26, SEQ ID NO:31, SEQ ID NO:32, SEQ ID NO:33, SEQ ID NO:34, SEQ ID NO:35 and SEQ ID NO:38 or a combination of two or more thereof is used in combination with a second amplification oligomer comprising, consisting or consisting essentially of a target hybridizing sequence as set forth in SEQ ID NO:7 together with a probe comprising, consisting or consisting essentially of a sequence selected from the group consisting of SEQ ID Nos. 4, 10, 17, 18, 19, 20, 21, 22, 23, 24, 29, 30, 36, 37, 39 and 40 or a combination of two or more thereof, preferably, SEQ ID No. 4.

According to another embodiment, a first amplification oligomer comprising, consisting or consisting essentially of a target hybridizing sequence selected from the group consisting of SEQ ID NO: 1, SEQ ID NO: 5, SEQ ID NO:11, SEQ ID NO:12, SEQ ID NO:25, SEQ ID NO:26, SEQ ID NO:31, SEQ ID NO:32, SEQ ID NO:33, SEQ ID NO:34, SEQ ID NO:35 and SEQ ID NO:38 or a combination of two or more thereof is used in combination with a second amplification oligomer comprising, consisting or consisting essentially of a target hybridizing sequence as set forth in SEQ ID NO:8 together with a probe comprising, consisting or consisting essentially of a sequence selected from the group consisting of SEQ ID Nos. 4, 10, 17, 18, 19, 20, 21, 22, 23, 24, 29, 30, 36, 37, 39 and 40 or a combination of two or more thereof, preferably, SEQ ID No. 4.

According to another embodiment, a first amplification oligomer comprising, consisting or consisting essentially of a target hybridizing sequence selected from the group consisting of SEQ ID NO: 1, SEQ ID NO: 5, SEQ ID NO:11, SEQ ID NO:12, SEQ ID NO:25, SEQ ID NO:26, SEQ ID NO:31, SEQ ID NO:32, SEQ ID NO:33, SEQ ID NO:34, SEQ ID NO:35 and SEQ ID NO:38 or a combination of two or more thereof is used in combination with a second amplification oligomer comprising, consisting or consisting essentially of a target hybridizing sequence as set forth in SEQ ID NO:9 together with a probe comprising, consisting or consisting essentially of a sequence selected from the group consisting of SEQ ID Nos. 4, 10, 17, 18, 19, 20, 21, 22, 23, 24, 29, 30, 36, 37, 39 and 40 or a combination of two or more thereof, preferably, SEQ ID No. 4.

According to another embodiment, a first amplification oligomer comprising, consisting or consisting essentially of a target hybridizing sequence selected from the group consisting of SEQ ID NO: 1, SEQ ID NO: 5, SEQ ID NO:11, SEQ ID NO:12, SEQ ID NO:25, SEQ ID NO:26, SEQ ID NO:31, SEQ ID NO:32, SEQ ID NO:33, SEQ ID NO:34, SEQ ID NO:35 and SEQ ID NO:38 or a combination of two or more thereof is used in combination with a second amplification oligomer comprising, consisting or consisting essentially of a target hybridizing sequence as set forth in SEQ ID NO:13 together with a probe comprising, consisting or consisting essentially of a sequence selected from the group consisting of SEQ ID Nos. 4, 10, 17, 18, 19, 20, 21, 22, 23, 24, 29, 30, 36, 37, 39 and 40 or a combination of two or more thereof, preferably, with a probe comprising, consisting or consisting essentially of a sequence selected from the group consisting of SEQ ID Nos 17 to 24 or a combination thereof.

According to another embodiment, a first amplification oligomer comprising, consisting or consisting essentially of a target hybridizing sequence selected from the group consisting of SEQ ID NO: 1, SEQ ID NO: 5, SEQ ID NO:11, SEQ ID NO:12, SEQ ID NO:25, SEQ ID NO:26, SEQ ID NO:31, SEQ ID NO:32, SEQ ID NO:33, SEQ ID NO:34, SEQ ID NO:35 and SEQ ID NO:38 or a combination of two or more thereof is used in combination with a second amplification oligomer comprising, consisting or consisting essentially of a target hybridizing sequence as set forth in SEQ ID NO:14 together with a probe comprising, consisting or consisting essentially of a sequence selected from the group consisting of SEQ ID Nos. 4, 10, 17, 18, 19, 20, 21, 22, 23, 24, 29, 30, 36, 37, 39 and 40 or a combination of two or more thereof, preferably, with a probe comprising, consisting or consisting essentially of a sequence selected from the group consisting of SEQ ID Nos 17 to 24 or or a combination of two or more thereof.

According to another embodiment, a first amplification oligomer comprising, consisting or consisting essentially of a target hybridizing sequence selected from the group consisting of SEQ ID NO: 1, SEQ ID NO: 5, SEQ ID NO:11, SEQ ID NO:12, SEQ ID NO:25, SEQ ID NO:26, SEQ ID NO:31, SEQ ID NO:32, SEQ ID NO:33, SEQ ID NO:34, SEQ ID NO:35 and SEQ ID NO:38 or a combination of two or more thereof is used in combination with a second amplification oligomer comprising, consisting or consisting essentially of a target hybridizing sequence as set forth in SEQ ID NO:15 together with a probe comprising, consisting or consisting essentially of a sequence selected from the group consisting of SEQ ID Nos. 4, 10, 17, 18, 19, 20, 21, 22, 23, 24, 29, 30, 36, 37, 39 and 40 or a combination of two or more thereof, preferably, with a probe comprising, consisting or consisting essentially of a sequence selected from the group consisting of SEQ ID Nos 17 to 24 or a combination of two or more thereof.

According to another embodiment, a first amplification oligomer comprising, consisting or consisting essentially of a target hybridizing sequence selected from the group consisting of SEQ ID NO: 1, SEQ ID NO: 5, SEQ ID NO:11, SEQ ID NO:12, SEQ ID NO:25, SEQ ID NO:26, SEQ ID NO:31, SEQ ID NO:32, SEQ ID NO:33, SEQ ID NO:34, SEQ ID NO:35 and SEQ ID NO:38 or a combination of two or more thereof is used in combination with a second amplification oligomer comprising, consisting or consisting essentially of a target hybridizing sequence as set forth in SEQ ID NO:16 together with a probe comprising, consisting or consisting essentially of a sequence selected from the group consisting of SEQ ID Nos. 4, 10, 17, 18, 19, 20, 21, 22, 23, 24, 29, 30, 36, 37, 39 and 40 or a combination of two or more thereof, preferably, with a probe comprising, consisting or consisting essentially of a sequence selected from the group consisting of SEQ ID Nos 17 to 24 or a combination of two or more thereof.

According to another embodiment, a first amplification oligomer comprising, consisting or consisting essentially of a target hybridizing sequence selected from the group consisting of SEQ ID NO: 1, SEQ ID NO: 5, SEQ ID NO:11, SEQ ID NO:12, SEQ ID NO:25, SEQ ID NO:26, SEQ ID NO:31, SEQ ID NO:32, SEQ ID NO:33, SEQ ID NO:34, SEQ ID NO:35 and SEQ ID NO:38 or a combination of two or more thereof is used in combination with a second amplification oligomer comprising, consisting or consisting essentially of a target hybridizing sequence as set forth in SEQ ID NO:27. together with a probe comprising, consisting or consisting essentially of a sequence selected from the group consisting of SEQ ID Nos. 4, 10, 17, 18, 19, 20, 21, 22, 23, 24, 29, 30, 36, 37, 39 and 40 or a combination of two or more thereof, preferably, with a probe comprising, consisting or consisting essentially of SEQ ID No 29 or 30 or a combination thereof.

According to another embodiment, a first amplification oligomer comprising, consisting or consisting essentially of a target hybridizing sequence selected from the group consisting of SEQ ID NO: 1, SEQ ID NO: 5, SEQ ID NO:11, SEQ ID NO:12, SEQ ID NO:25, SEQ ID NO:26, SEQ ID NO:31, SEQ ID NO:32, SEQ ID NO:33, SEQ ID NO:34, SEQ ID NO:35 and SEQ ID NO:38 or a combination of two or more thereof is used in combination with a second amplification oligomer comprising, consisting or consisting essentially of a target hybridizing sequence as set forth in SEQ ID NO:28 together with a probe comprising, consisting or consisting essentially of a sequence selected from the group consisting of SEQ ID Nos. 4, 10, 17, 18, 19, 20, 21, 22, 23, 24, 29, 30, 36, 37, 39 and 40 or a combination of two or more thereof, preferably, with a probe comprising, consisting or consisting essentially of SEQ ID No 29 or 30 or a combination thereof.

Preferred Combinations and Compositions for the Amplification and/or Detection of Adenovirus In one preferred embodiment, a first amplification oligomer comprising, consisting or consisting essentially of a target hybridizing sequence as set forth in SEQ ID NO: 5 is used in combination with at least one second amplification oligomer comprising, consisting or consisting essentially of a target hybridizing sequence selected from the group consisting of SEQ ID NO: 6, SEQ ID NO: 7, SEQ ID NO:8 and SEQ ID NO: 9 or a combination of two or more thereof. According to a further preferred embodiment, any of these combinations are used together with at least one probe comprising, consisting or consisting essentially of the sequence set forth in SEQ ID No. 10.

In another preferred embodiment, a first amplification oligomer comprising, consisting or consisting essentially of a target hybridizing sequence as set forth in SEQ ID NO: 11 is used in combination with at least one second amplification oligomer comprising, consisting or consisting essentially of a target hybridizing sequence selected from the group consisting of SEQ ID NO: 13, SEQ ID NO: 14, SEQ ID NO: 15 and SEQ ID NO: 16 or a combination of two or more thereof. According to a further preferred embodiment, any of these combinations are used together with at least one probe comprising, consisting or consisting essentially of the sequence set forth in SEQ ID No. 19 or SEQ ID No. 20 or a combination thereof.

In another preferred embodiment, a first amplification oligomer comprising, consisting or consisting essentially of a target hybridizing sequence as set forth in SEQ ID NO: 12 is used in combination with at least one second amplification oligomer comprising, consisting or consisting essentially of a target hybridizing sequence a selected from the group consisting of SEQ ID NO: 13, SEQ ID NO: 14, SEQ ID NO: 15 and SEQ ID NO: 16 or a combination of two or more thereof. According to a further preferred embodiment, any of these combinations are used together with at least one probe comprising, consisting or consisting essentially of the sequence set forth in SEQ ID No. 19 or SEQ ID No. 20 or a combination thereof.

In another preferred embodiment, a first amplification oligomer comprising, consisting or consisting essentially of a target hybridizing sequence as set forth in SEQ ID NO: 12 is used in combination with at least one second amplification oligomer comprising, consisting or consisting essentially of a target hybridizing sequence as set forth in SEQ ID NO: 15 or SEQ ID NO: 16 or a combination thereof. According to a further preferred embodiment, this combination is used together with at least one probe comprising, consisting or consisting essentially of a sequence selected from the group consisting of SEQ ID No. 21, SEQ ID No. 22, SEQ ID No. 23 and SEQ ID No. 24 or a combination of two or more thereof.

In another preferred embodiment, a first amplification oligomer comprising, consisting or consisting essentially of a target hybridizing sequence as set forth in SEQ ID NO: 25 or SEQ ID NO: 26 or a combination thereof is used in combination with at least one second amplification oligomer comprising, consisting or consisting essentially of a target hybridizing sequence as set forth in SEQ ID NO: 27 or SEQ ID NO: 28 or a combination thereof (eg. SEQ ID Nos. 25, 26, 27 and 28; SEQ ID Nos. 26, 27 and 28; SEQ ID Nos. 25, 27 and 28; SEQ ID Nos. 25, 26 and 28; SEQ ID Nos. 25, 26 and 27). According to a further preferred embodiment, any one or more of these combinations can be used together with at least one probe comprising, consisting or consisting essentially of the sequence selected from the group consisting of SEQ ID No. 21, SEQ ID No. 22, SEQ ID No. 23, SEQ ID No. 24, SEQ ID No. 29 and SEQ ID No. 30 or a combination of two or more thereof.

In another preferred embodiment, a first amplification oligomer comprising, consisting or consisting essentially of a target hybridizing sequence as set forth in SEQ ID NO: 31 or SEQ ID NO: 26 or a combination thereof is used in combination with at least one second amplification oligomer comprising, consisting or consisting essentially of a target hybridizing sequence as set forth in SEQ ID NO: 27 or SEQ ID NO: 28 or a combination thereof. According to a further preferred embodiment, any one or more of these combinations can be used together with at least one probe comprising, consisting or consisting essentially of the sequence selected from the group consisting of SEQ ID No. 21, SEQ ID No. 22, SEQ ID No. 23 and SEQ ID No. 24 or a combination of two or more thereof.

In another preferred embodiment, a first amplification oligomer comprising, consisting or consisting essentially of a target hybridizing sequence selected from the group consisting of SEQ ID NO: 33, SEQ ID NO: 34 and SEQ ID NO: 35 or a combination of two or more thereof (eg. SEQ ID Nos. 33 and 35 or 34 and 35) is used in combination with at least one second amplification oligomer comprising, consisting or consisting essentially of a target hybridizing sequence as set forth in SEQ ID NO: 27 or SEQ ID NO: 28 or a combination thereof. According to a further preferred embodiment, any one or more of these combinations can be used together with at least one probe comprising, consisting or consisting essentially of the sequence selected from the group consisting of SEQ ID No. 21, SEQ ID No. 22, SEQ ID No. 23 and SEQ ID No. 24 or a combination of two or more thereof.

In another preferred embodiment, a first amplification oligomer comprising, consisting or consisting essentially of a target hybridizing sequence as set forth in SEQ ID NO: 25 or SEQ ID NO: 26 or a combination of two or more thereof is used in combination with at least one second amplification oligomer comprising, consisting or consisting essentially of SEQ ID NO: 27 or SEQ ID NO: 28 or a combination thereof (eg. SEQ ID Nos 25, 26, 27 and 28; SEQ ID Nos 26, 27 and 28; SEQ ID Nos 25, 26 and 28; SEQ ID Nos 25, 26 and 27; SEQ ID Nos 25, 27 and 28; SEQ ID Nos 25 and 27; SEQ ID Nos 25 and 28; SEQ ID Nos 26 and 27 and SEQ ID Nos 26 and 28). According to a further preferred embodiment, any one or more of these combinations can be used together with at least one probe comprising, consisting or consisting essentially of the sequence set forth in SEQ ID No. 36 or SEQ ID No. 37 or a combination thereof. Thus, for example, a particular preferred combination is any of SEQ ID Nos 25, 26, 27 and 28; SEQ ID Nos 26, 27 and 28; SEQ ID Nos 25, 26 and 28; SEQ ID Nos 25, 26 and 27; SEQ ID Nos 25, 27 and 28; SEQ ID Nos 25 and 27; SEQ ID Nos 25 and 28; SEQ ID Nos 26 and 27 and SEQ ID Nos 26 and 28 in combination with SEQ ID No. 36 and/or SEQ ID No. 37.

Sample Preparation

Preparation of samples for amplification and detection of Adenovirus sequences may include methods of separating and/or concentrating viruses contained in a sample from other sample components. Sample preparation may include routine methods of disrupting samples or lysing samples to release intracellular contents, including Adenovirus nucleic acids or genetic sequences comprising Adenovirus nucleic acid. Sample preparation before amplification may include an optional step of target capture to specifically or non-specifically separate the target nucleic acids from other sample components. Nonspecific target capture methods may involve selective precipitation of nucleic acids from a substantially aqueous mixture, adherence of nucleic acids to a support that is washed to remove other sample components, other methods of physically separating nucleic acids from a mixture that contains Adenovirus nucleic acid and other sample components.

Amplification of the Adenovirus Target Region

Amplifying the Adenovirus target region using two or more primers may be accomplished using a variety of known nucleic acid amplification reactions. For example, amplification may be achieved using PCR amplification (U.S. Pat. Nos. 4,683,195, 4,683,202, and 4,800,159, Mullis et al.) to produce multiple DNA strands by using thermocycling reactions that separate dsDNA and primers specific for portions of the separated strands to make additional dsDNA molecules by using a DNA polymerase. Well known variations of the basic PCR method may also be used, e.g., PCR coupled with real-time detection—such as Taqman PCR. One disadvantage of PCR is the need of a thermocycler to heat and cool the amplification mixture to denature the DNA. As well as PCR, a variety of other techniques have been developed for detection and amplification of specific sequences. One example is the ligase chain reaction (LCR). In addition to conventional methods of DNA amplification that rely on the thermal denaturation of the target during the amplification reaction, a number of methods have been described that do not require template denaturation during the amplification reaction and are thus termed isothermal amplification technologies. Examples of isothermal amplification are Strand Displacement Amplification (SDA), Transcription Mediated Amplification (TMA) and Nucleic Acid Sequence Based Amplification (NASBA) that use an RNA polymerase to copy RNA sequences but not corresponding genomic DNA. Other DNA-based isothermal techniques include Rolling Circle Amplification (RCA), Ramification Amplification (RAM) and Helicase-Dependent isothermal DNA amplification (HDA).

In one embodiment, the amplification method is TMA. A TMA-based assay produces many RNA transcripts (amplicons) from a single copy of target nucleic acid and the amplicons are detected to indicate the presence of the target Adenovirus in the sample. Briefly, in TMA-based assays, a promoter-primer hybridizes specifically to the target sequence and reverse transcriptase (RT) that includes RNaseH activity creates a first strand cDNA by extension from the 3' end of the promoter-primer and digests the template strand. The cDNA is then bound by a second primer and a new strand of DNA is synthesized from the end of the second primer using RT to create a double-stranded DNA (dsDNA) containing a functional promoter sequence. RNA polymerase specific for that promoter binds to the promoter sequence and multiple RNA transcripts are produced, which each can act as a template for additional sequence replication using the same steps used for the initial template. Thus, large amounts of single-stranded amplified product are made using substantially isothermal reaction conditions.

Amplification methods that use TMA amplification may include the following steps. Briefly, a target nucleic acid containing the target sequence to be amplified is provided. A first amplification oligomer is brought in contact with that target nucleic acid by hybridizing to the target sequence. The first amplification oligomer may be a primer or a promoter primer. A suitable nucleic acid polymerase then generates a nucleic acid strand amplification product that is complementary to the target nucleic acid target sequence. Using a primer as the first amplification oligomer, then the second amplification oligomer is a promoter primer or promoter provider. A suitable nucleic acid polymerase uses the newly generated amplification product to which the promoter-based oligomer is hybridized as a primer to make a complementary strand of the unhybridized promoter sequence. If the second amplification oligomer is a promoter primer, then a complementary copy of the amplification product hybridized by the second amplification oligomer is also generated. The now double stranded promoter sequence of the promoter-based amplification is used by a suitable RNA polymerase to initiate transcription and make RNA transcript amplification products. The first amplification oligomer primer can then hybridize the transcribed amplification products and the steps can repeat. When the target nucleic acid is DNA the first amplification oligomer is a promoter primer and the second amplification is a primer. Amplification generally proceeds as described above, and as is described in the art. See e.g., U.S. Pat. Nos. 4,868,105; 5,124,246; 5,130,238; 5,399,491; 5,437,990; 5,554,516; and 7,374,885; and PCT Pub. Nos. WO 88/01302; WO 88/10315 and WO 95/03430 describing TMA and other variations of transcription-associated amplification. The amplified products may be detected in real-time during amplification, or at the end of the amplification reaction. Detection may be performed by a number of methods. Probe-based detection methods use an oligonucleotide probe comprising a target hybridizing sequence that binds specifically to a target sequence contained in the amplification products. Detection of a signal resulting from the bound probes indicates the presence of the target nucleic acid in the sample.

Nucleic Acid Detection

Detection of the nucleic acids may be accomplished by a variety of methods. Detection methods may use nucleic acid probes comprising a target hybridizing sequence that is complementary to a portion of the amplified product and detecting the presence of the probe:product complex, or by using a complex of probes that may amplify the detectable signal associated with the amplified products (e.g., U.S. Pat. Nos. 5,424,413; 5,451,503; and 5,849,481). Directly or indirectly labeled probes that specifically associate with the amplified product provide a detectable signal that indicates the presence of the target nucleic acid in the sample. For example, if the target nucleic acid is Adenovirus DNA, the amplified product will contain a sequence in or complementary to an Adenovirus target sequence. A probe is configured to bind directly or indirectly to a portion of the amplification product to indicate the presence of Adenovirus in the tested sample.

Amplified products may be detected in real-time during amplification, or at the end of the amplification reaction. Detection may be performed by a number of methods. Probe-based detection methods use an oligonucleotide probe comprising a target hybridizing sequence that binds specifically to a target sequence contained in the amplification products. Detection of a signal resulting from the bound probes indicates the presence of the target nucleic acid in the sample.

Essentially any labeling and detection system that can be used for monitoring specific nucleic acid hybridization can be used in conjunction with the present invention. Included among the collection of useful labels are radiolabels, enzymes, haptens, linked oligonucleotides, chemi luminescent molecules, fluorescent moieties (either alone or in combination with "quencher" moieties), and redox-active moieties that are amenable to electronic detection methods. Preferred chemiluminescent molecules include acridinium esters of the type disclosed by Arnold et al., in U.S. Pat. No. 5,283,174 for use in connection with homogenous protection assays, and of the type disclosed by Woodhead et al., in U.S. Pat. No. 5,656,207 for use in connection with assays that quantify multiple targets in a single reaction. Electronic labeling and detection approaches are disclosed in U.S. Pat. Nos. 5,591,578 and 5,770,369, and the published international patent application WO 98/57158.

Redox active moieties useful as labels include transition metals such as Cd, Mg, Cu, Co, Pd, Zn, Fe and Ru. Particularly preferred detectable labels for probes in accordance with the present invention are detectable in homogeneous assay systems (i.e., where, in a mixture, bound labeled probe exhibits a detectable change, such as stability or differential degradation, compared to unbound labeled probe). While other homogeneously detectable labels, such as fluorescent labels and electronically detectable labels, are intended for use in the practice of the present invention, a preferred label for use in homogenous assays is a chemiluminescent compound (e.g., as described by Woodhead et al., in U.S. Pat. No. 5,656,207; by Nelson et al., in U.S. Pat. No. 5,658,737; or by Arnold et al., in U.S. Pat. No. 5,639,604). Chemiluminescent labels may include acridinium ester ("AE") compounds, such as standard AE or derivatives thereof, such as naphthyl-AE, ortho-AE, 1- or 3-methyl-AE, 2,7-dimethyl-AE, 4,5-dimethyl-AE, ortho-dibromo-AE, ortho-dimethyl-AE, meta-dimethyl-AE, ortho-methoxy-AE, ortho-methoxy(cinnamyl)-AE, ortho-methyl-AE, ortho-fluoro-AE, 1- or 3-methyl-ortho-fluoro-AE, 1- or 3-methyl-meta-difluoro-AE, and 2-methyl-AE.

Another example of a hybridization assay probe that may be used in conjunction with the invention is a structure commonly referred to as a "Molecular Beacon." Molecular Beacons comprise nucleic acid molecules having a target complementary sequence, an affinity pair (or nucleic acid arms) holding the probe in a closed conformation in the absence of a target nucleic acid sequence, and a label pair that interacts when the probe is in a closed conformation. Hybridization of the target nucleic acid and the target complementary sequence separates the members of the affinity pair, thereby shifting the probe to an open conformation. The shift to the open conformation is detectable due to reduced interaction of the label pair, which may be, for example, a fluorophore and a quencher (e.g., DABCYL and EDANS). Molecular Beacons are fully described in U.S. Pat. No. 5,925,517. Molecular beacons useful for detecting Adenovirus-specific nucleic acid sequences may be created by appending to either end of one of the probe sequences disclosed herein, a first nucleic acid arm comprising a fluorophore and a second nucleic acid arm comprising a quencher moiety. In this configuration, the Adenovirus-specific probe sequence disclosed herein serves as the target-complementary "loop" portion of the resulting molecular beacon.

Molecular beacons preferably are labeled with an interactive pair of detectable labels. Examples of detectable labels that are preferred as members of an interactive pair of labels interact with each other by FRET or non-FRET energy transfer mechanisms. Fluorescence resonance energy transfer (FRET) involves the radiationless transmission of energy quanta from the site of absorption to the site of its utilization in the molecule, or system of molecules, by resonance interaction between chromophores, over distances considerably greater than interatomic distances, without conversion to thermal energy, and without the donor and acceptor coming into kinetic collision. The "donor" is the moiety that initially absorbs the energy, and the "acceptor" is the moiety to which the energy is subsequently transferred, hi addition to FRET, there are at least three other "non-FRET" energy transfer processes by which excitation energy can be transferred from a donor to an acceptor molecule.

When two labels are held sufficiently close that energy emitted by one label can be received or absorbed by the second label, whether by a FRET or non-FRET mechanism, the two labels are said to be in "energy transfer relationship" with each other. This is the case, for example, when a molecular beacon is maintained in the closed state by formation of a stem duplex, and fluorescent emission from a fluorophore attached to one arm of the probe is quenched by a quencher moiety on the opposite arm.

Highly preferred label moieties for the molecular beacons include a fluorophore and a second moiety having fluorescence quenching properties (i.e., a "quencher"). In this embodiment, the characteristic signal is likely fluorescence of a particular wavelength, but alternatively could be a visible light signal. When fluorescence is involved, changes in emission are preferably due to FRET, or to radiative energy transfer or non-FRET modes. When a molecular beacon having a pair of interactive labels in the closed state is stimulated by an appropriate frequency of light, a fluorescent signal is generated at a first level, which may be very low. When this same probe is in the open state and is stimulated by an appropriate frequency of light, the fluorophore and the quencher moieties are sufficiently separated from each other that energy transfer between them is substantially precluded. Under that condition, the quencher moiety is unable to quench the fluorescence from the fluorophore moiety. If the fluorophore is stimulated by light energy of an appropriate wavelength, a fluorescent signal of a second level, higher than the first level, will be generated. The difference between the two levels of fluorescence is detectable and measurable. Using fluorophore and quencher moieties in this manner, the molecular beacon is only "on" in the "open" conformation and indicates that the probe is bound to the target by emanating an easily detectable signal. The conformational state of the probe alters the signal generated from the probe by regulating the interaction between the label moieties. Examples of donor/acceptor label pairs that may be used in connection with the invention, include fluorescein/tetramethylrhodamine, EDANS/fluororescein, EDANS/DABCYL, coumarin/DABCYL, fluorescein/fluorescein, BODIPY FL/BODIPY FL, fluorescein/DABCYL, lucifer yellow/DABCYL, BODIPY/DABCYL, eosine/DABCYL, erythrosine/DABCYL, tetramethylrhodamine/DABCYL, Texas Red/DABCYL, CY5/BH1, CY5/BH2, CY3/BH1, CY3/BH2, fluorescein/QSY7, FAM/BHQ1 and Quasar/BHQ1. Those having an ordinary level of skill in the art will understand that when donor and acceptor dyes are different, energy transfer can be detected by the appearance of sensitized fluorescence of the acceptor or by quenching of donor fluorescence. When the donor and acceptor species are the same, energy can be detected by the resulting fluorescence depolarization. Non-fluorescent acceptors such as DABCYL and the QSY 7 dyes advantageously eliminate the potential problem of background fluorescence resulting from direct (i.e., non-sensitized) acceptor excitation. Preferred fluorophore moieties that can be used as one member of a donor-acceptor pair include fluorescein, ROX, and the CY dyes (such as CY5).

Synthetic techniques and methods of bonding labels to nucleic acids and detecting labels are well known in the art (e.g., see Sambrook et al., Molecular Cloning. A Laboratory Manual. 2nd ed. (Cold Spring Harbor Laboratory Press, Cold Spring Harbor, N.Y., 1989), Chapter 10; Nelson et al., U.S. Pat. No. 5,658,737; Woodhead et al., U.S. Pat. No. 5,656,207; Hogan et al., U.S. Pat. No. 5,547,842; Arnold et al., U.S. Pat. No. 5,283,174; Kourilsky et al., U.S. Pat. No. 4,581,333), and Becker et al., European Patent App. No. 0 747 706.

Probes that hybridize to the amplified sequences include hairpin oligonucleotides such as Molecular Torches and linear oligonucleotides that substantially do not form conformations held by intramolecular bonds. Preferably, said probes may include labels. Linear probe embodiments may include a chemiluminescent compound as the label, e.g. a chemiluminescent AE compound attached to the probe sequence via a linker (substantially as described in U.S. Pat. Nos. 5,585,481 and 5,639,604, particularly at column 10, line 6 to column 11, line 3, and in Example 8 therein). Examples of labeling positions are a central region of the probe oligomer and near a region of A:T base pairing, at a 3' or 5' terminus of the oligomer, and at or near a mismatch site with a known sequence that is not the desired target sequence. Hairpin or linear probes may be labeled with any of a variety of different types of interacting labels, where one interacting member is usually attached to the 5' end of the probe and the other interacting member is attached to the 3' end of the probe. Dye labeled probes, including dual labeled probes, single labeled probes, AE labeled probes and the like, are generally known. Dual labeled probes can be labeled at one end with a fluorescent label ("F") that absorbs light of a particular wavelength or range and emits light another emission wavelength or range and at the other end with a quencher ("Q") that dampens, partially or completely, signal emitted from the excited F when Q is in proximity with the fluorophore. Such a probe may be referred to as labeled with a fluorescent/quencher (F/Q) pair. One embodiment of a hairpin probe is a "molecular torch" that detects an amplified product to indicate whether a target sequence is present in the sample after the amplification step. A molecular torch probe comprises a target binding domain and a closing domain, as is described above. These domains allow the molecular torch to exist in open and closed conformations, depending on whether the torch is bound to a target. (See also, U.S. Pat. Nos. 6,849,412; 6,835,542; 6,534,274; and 6,361,945). Another hairpin probe embodiment is a "molecular beacon" which is generally described in Tyagi et al., 1998, Nature Biotechnol. 16:49-53, and in U.S. Pat. Nos. 5,118,801; and 5,312,728. Methods for using such hairpin probes to detect the presence of a target sequence are well known in the art.

The methods for amplifying a target nucleic acid sequence present in the nucleic acid of Adenovirus can therefore include an optional further step for detecting amplicons. This procedure preferably involves a step for contacting a test sample with a hybridization assay probe that preferentially hybridizes to the target nucleic acid sequence, or the complement thereof, under stringent hybridization conditions, thereby forming a probe:target duplex that is stable for detection. Next there is a step for determining whether the hybrid is present in the test sample as an indication of the presence or absence of Adenovirus nucleic acids in the test sample. This may involve detecting the probe:target duplex, and preferably involves homogeneous assay systems.

Hybridization assay probes useful for detecting Adenovirus nucleic acid sequences include a sequence of bases substantially complementary to a Adenovirus target nucleic acid sequence. Thus, probes of the invention hybridize one strand of a Adenovirus target nucleic acid sequence, or the complement thereof. These probes may optionally have additional bases outside of the targeted nucleic acid region which may or may not be complementary to Adenovirus nucleic acid.

Preferred probes are sufficiently homologous to the target nucleic acid to hybridize under stringent hybridization conditions corresponding to about 42° C., or more preferably about 60° C. when the salt concentration is in the range of 0.6-0.9 M. Preferred salts include lithium chloride, but other salts such as sodium chloride and sodium citrate also can be used in the hybridization solution. Example high stringency hybridization conditions are alternatively provided by about 42° C., or more preferably about 60° C., and 0.48 M sodium phosphate buffer, 0.1% sodium dodecyl sulfate, and 1 mM each of EDTA and EGTA, or by 0.6 M LiCl, 1% lithium lauryl sulfate, 60 mM lithium succinate and 10 mM each of EDTA and EGTA. Probes in accordance with the invention have sequences complementary to, or corresponding to different domains of the Adenovirus genome. Certain probes that are preferred for detecting Adenovirus nucleic acid sequences have a probe sequence, which includes the target-complementary sequence of bases together with any base sequences that are not complementary to the nucleic acid that is to be detected, in the length range of from 10-100 nucleotides. Probes for detecting Adenovirus nucleic acid sequences have target-complementary sequences in the length range of from 15-30, from 16-24, from 18-22 or from 18-20 nucleotides. Of course, these target-complementary sequences may be linear sequences, or may be contained in the structure of a molecular beacon or other construct having one or more optional nucleic acid sequences that are non-complementary to the Adenovirus target sequence that is to be detected. As indicated above, probes may be made of DNA, RNA, a combination DNA and RNA, a nucleic acid analog, or contain one or more modified nucleosides (e.g., a ribonucleoside having a 2'-O-methyl substitution to the ribofuranosyl moiety).

Kits

The oligomers for use in the methods described herein are suited for preparation of kits. Such a kit may comprise containers, each with one or more of the various oligomers optionally together with one or more of the reagents (eg. enzymes) required to perform the methods described herein. The components of the kit may be supplied in concentrated form. A set of instructions for using the components of the kit will also typically be included. Where the kit comprises combinations of oligomers then the individual oligomers may be provided in individual form, with appropriate instructions for mixing same, or combinations thereof that are ready mixed.

In one aspect, there is provided a kit comprising the composition of the present invention and optionally a set of instructions for performing same. In one embodiment, this composition comprises a first amplification oligomer comprising, consisting or consisting essentially of a target hybridizing sequence as set forth in SEQ ID NO: 25 or SEQ ID NO: 26 or a combination of two or more thereof in combination with at least one second amplification oligomer comprising, consisting or consisting essentially of SEQ ID NO: 27 or SEQ ID NO: 28 or a combination thereof. Accordingly, the composition may comprise SEQ ID Nos 25, 26, 27 and 28; SEQ ID Nos 26, 27 and 28; SEQ ID Nos 25, 26 and 28; SEQ ID Nos 25, 26 and 27; SEQ ID Nos 25, 27 and 28; SEQ ID Nos 25 and 27; SEQ ID Nos 25 and 28; SEQ ID Nos 26 and 27 and SEQ ID Nos 26 and 28. According to a further preferred embodiment, the composition may comprise any one or more of these combinations together with at least one probe comprising, consisting or consisting essentially of the sequence set forth in SEQ ID No. 36 or SEQ ID No. 37 or a combination thereof. Thus, for example, a particular preferred combination is any of SEQ ID Nos 25, 26, 27 and 28; SEQ ID Nos 26, 27 and 28; SEQ ID Nos 25, 26 and 28; SEQ ID Nos 25, 26 and 27; SEQ ID Nos 25, 27 and 28; SEQ ID Nos 25 and 27; SEQ ID Nos 25 and 28; SEQ ID Nos 26 and 27 and SEQ ID Nos 26 and 28 in combination with SEQ ID No. 36 and/or SEQ ID No. 37.

Correlation of Detection of a Target Sequence with Diagnosis

The detection of amplified target sequences characteristic of Adenovirus in a biological sample from an individual is indicative of infection by Adenovirus.

EXAMPLES

Example 1

Analysis of Amplification Primers and Probes

Materials & Methods

In a first amplification reaction, the following was used: Fast Start Master Buffer (Roche) at 1× to 2× concentration, 2 Units of Fast Start Taq DNA polymerase (Roche), 100 nM of a forward amplification primer (SEQ ID No. 5) and 100 nM of a reverse amplification primer (SEQ ID No. 6 or SEQ ID No. 8) and 100 nM probe (SEQ ID No. 10).

The total reaction volume was 20 microlitres with 5 microlitres of template nucleic acid extracted from Adenovirus added per reaction. Control reactions were performed by setting up a reaction as described above but not adding any template nucleic acids. The amplification cycles used were as follows for both sets of amplification reactions: Hold for 600 seconds at 95 deg. C. with optics off; 95 deg. C. for 30 seconds with optics off and 55 deg. C. for 60 seconds with optics on (5 cycles); 95 deg. C. for 10 seconds with optics off and 55 deg. C. for 60 seconds (40 cycles) with optics on.

Results

TABLE 1

Adenovirus Amplification and Detection with Primer and Probe Sets

|  | SEQ ID Nos. 5, 6 and 10 | | SEQ ID Nos. 5, 8 and 10 | |
| --- | --- | --- | --- | --- |
|  | $C_T$ | RFU | $C_T$ | RFU |
| Target/Sample | 26.9 | 519 | 26.4 | 383 |

The results are presented as $C_T$/RFU (cycle threshold/relative fluorescent unit) values and represent the average of 12 experiments using various Adenovirus serotypes. Amplification was not seen in any of the control reactions.

Conclusion

The primers and probes used appeared to be sensitive and specific for Adenovirus nucleic acid.

Example 2

Analysis of Further Amplification Primers and Probes

Materials & Methods

The following reagents were used: Fast Start Master Buffer (Roche) at 1× to 2× concentration, 2 Units of Fast Start Taq DNA polymerase (Roche), 200 nM of a forward amplification primer (SEQ ID No. 11 or SEQ ID No. 12) and 200 nM of a reverse amplification primer (SEQ ID No. 13 or SEQ ID No: 15) and 200 nM probe (SEQ ID No. 17 or SEQ ID No. 19).

The total reaction volume was 20 microlitres with 5 microlitres of template nucleic acid extracted from Adenovirus added per reaction. Control reactions were performed by setting up a reaction as described above but not adding any template nucleic acids. The amplification cycles used were as follows: Hold for 600 seconds at 95 deg. C. with optics off; 95 deg. C. for 30 seconds with optics off and 55 deg. C. for 60 seconds with optics on (5 cycles); 95 deg. C. for 10 seconds with optics off and 55 deg. C. for 60 seconds (40 cycles) with optics on.

Results

TABLE 2

Adenovirus Amplification and Detection with Primer and Probe Sets

|  | SEQ ID Nos. 11, 13 and 17 | | SEQ ID Nos. 11, 13 and 19 | |
| --- | --- | --- | --- | --- |
|  | $C_T$ | RFU | $C_T$ | RFU |
| Target/Sample | 8.7 | 29.8 | 32 | 460 |

|  | SEQ ID Nos. 11, 15 and 17 | | SEQ ID Nos. 11, 15 and 19 | |
| --- | --- | --- | --- | --- |
|  | $C_T$ | RFU | $C_T$ | RFU |
| Target/Sample | 13.3 | 29.5 | 32.3 | 406.4 |

|  | SEQ ID Nos. 12, 15 and 19 | | SEQ ID Nos. 12, 15 and 17 | |
| --- | --- | --- | --- | --- |
|  | $C_T$ | RFU | $C_T$ | RFU |
| Target/Sample | 29.6 | 620 | 12.6 | 32.8 |

|  | SEQ ID Nos. 12, 13 and 19 | | SEQ ID Nos. 12, 13 and 17 | |
| --- | --- | --- | --- | --- |
|  | $C_T$ | RFU | $C_T$ | RFU |
| Target/Sample | 29.6 | 504 | 8.3 | 18.9 |

The results are presented as $C_T$/RFU values and represent the average of 8 experiments using various Adenovirus serotypes. Amplification was not seen in any of the control reactions.

Conclusion

Combinations of SEQ ID Nos. 11, 13 and 19, SEQ ID Nos. 11, 15 and 19, SEQ ID Nos. 12, 15 and 19 or SEQ ID Nos. 12, 13 and 19 were sensitive and specific for Adenovirus nucleic acid. The combinations comprising the SEQ ID No. 12 forward primer appears to have better sensitivity than the combination comprising the SEQ ID No. 11 forward primer. The combination comprising SEQ ID Nos. 12, 15 and 19 appeared to be most sensitive in these experiments.

Example 3

Adenovirus Serotype Analysis Using SEQ ID Nos. 12, 15 and 19

Materials & Methods

The following reagents used: Fast Start Master Buffer (Roche) at 1× concentration, 2 Units of Fast Start Taq DNA polymerase (Roche), 400 nM of a forward amplification primer (SEQ ID No. 12) and 400 nM of a reverse amplification primer (SEQ ID No. 15) was used together with 400 nM probe (SEQ ID No. 19). The total reaction volume was 20 microlitres with 5 microlitres of template nucleic acid extracted from Adenovirus added per reaction. Control reactions were set-up, but no template nucleic acid was added. The amplification cycles used were as follows: Hold for 600 seconds at 95 deg. C. with optics off; 95 deg. C. for 30 seconds with optics off and 55 deg. C. for 60 seconds with optics on (5 cycles); 95 deg. C. for 10 seconds with optics off and 55 deg. C. for 60 seconds (40 cycles) with optics on.

Results

TABLE 3

Adenovirus Serotype Analysis

| Serotype | $C_T$ | RFU |
| --- | --- | --- |
| 2-1 | 26 | 1203 |
| 4-1 | 31 | 666 |
| 6-1 | 29 | 926 |
| 7-1 | 32 | 605 |
| 9-1 | 26 | 1137 |
| 10-1 | 28 | 1252 |
| 11-1 | 28 | 630 |
| 12-1 | 26 | 1119 |
| 13-1 | 26 | 1100 |
| 14-1 | 30 | 682 |
| 15-1 | 26 | 1078 |
| 16-1 | 29 | 723 |
| 17-1 | 23 | 1100 |
| 18-1 | 34 | 387 |
| 19-1 | 27 | 1146 |
| 20-1 | 23 | 996 |
| 21-1 | 31 | 568 |
| 22-1 | 25 | 1044 |
| 23-1 | 23 | 1109 |
| 24-1 | 25 | 1221 |
| 25-1 | 32 | 836 |
| 26-1 | 24 | 1107 |
| 27-1 | 25 | 1070 |
| 28-1 | 26 | 989 |
| 29-1 | 27 | 1116 |
| 30-1 | 22 | 1166 |
| 31-1 | 21 | 1127 |
| 33-1 | 28 | 941 |
| 34-1 | 28 | 654 |
| 35-1 | 29 | 542 |
| 36-1 | 24 | 997 |
| 37-1 | 24 | 1125 |
| 38-1 | 26 | 1033 |
| 39-1 | 23 | 1143 |
| 40-1 | 27 | 1114 |
| 41-1 | 25 | 994 |
| 42-1 | 23 | 1125 |
| 43-1 | 22 | 1149 |
| 44-1 | 22 | 1141 |
| 45-1 | 27 | 1071 |
| 46-1 | 27 | 1047 |
| 47-1 | 22 | 1144 |
| 48-1 | 25 | 1174 |
| 49-1 | 26 | 1068 |
| 50-1 | 25 | 672 |
| 51-1 | 26 | 1099 |
| 1-1 | 29 | 956 |
| 3-1 | 32 | 540 |
| 5-1 | 29 | 791 |
| 7A-1 | 26 | 632 |
| 8-1 | 34 | 553 |
| 32-2 | 24 | 974 |

The Serotype column is set-up to reflect "serotype number-1×$10^x$ TCID$_{50}$/mL." $C_T$ values have all been rounded down. The results are presented as $C_T$/RFU values.

Conclusion

The combination of SEQ ID Nos. 12, 15 and 19 was able to detect all serotypes of Adenovirus that were tested.

Example 4

Analysis of Further Probe Combinations Together with SEQ ID No. 12 and 15 Primers Materials & Methods The following reagents used: Fast Start Master Buffer (Roche) at 1× concentration, 2 Units of Fast Start Taq DNA polymerase (Roche), 100 nM of a forward amplification primer (SEQ ID No. 12) and 100 nM of a reverse amplification primer (SEQ ID No. 15) was used together with either: 150 nM probe (SEQ ID No. 21) and 50 nM probe (SEQ ID No. 24); 100 nM probe (SEQ ID No. 21) and 100 nM probe (SEQ ID No. 24); 50 nM probe (SEQ ID No. 21) and 150 nM probe (SEQ ID No. 24). The total reaction volume was 20 microlitres with 5 microlitres of template nucleic acid extracted from Adenovirus added per reaction. Control reactions were set-up without the addition of template nucleic acid. The amplification cycles used were as follows: Hold for 600 seconds at 95 deg. C. with optics off; 95 deg. C. for 30 seconds with optics off and 55 deg. C. for 60 seconds with optics on (5 cycles); 95 deg. C. for 10 seconds with optics off and 55 deg. C. for 60 seconds (40 cycles) with optics on.

Results

TABLE 4

Amplification and detection using different concentrations of probe combinations

|  | 150 nM SEQ ID No. 21 and 50 nM SEQ ID No. 24; | | 100 nM SEQ ID No. 21 and 100 nM SEQ ID No. 24; | |
| --- | --- | --- | --- | --- |
|  | $C_T$ | RFU | $C_T$ | RFU |
| Target | 34.8 | 291 | 26.9 | 318 |

|  | 50 nM SEQ ID No. 21 and 150 nM SEQ ID No. 24 | |
| --- | --- | --- |
|  | $C_T$ | RFU |
| Target | 26.8 | 339 |

The results are presented as $C_T$/RFU values and represent the average of 6 experiments using various Adenovirus serotypes.

Conclusion

SEQ ID No. 21 and ID No. 24 probes in combination with SEQ ID No. 12 and 15 were able to sensitively and specifically detect Adenovirus at the various concentrations tested.

Example 5

Analysis of Further Probe and Primer Combinations for the Detection of Adenovirus Materials & Methods The following reagents used:

Fast Start Master Buffer (Roche) at 1× concentration, 2 Units of Fast Start Taq DNA polymerase (Roche) and either: (i) 50 mM of a forward amplification primer (SEQ ID No. 25), 50 mM of a forward amplification primer (SEQ ID No. 26), 50 mM of a reverse amplification primer (SEQ ID No. 27), 50 mM of a reverse amplification primer (SEQ ID No. 28) and 100 nM of probes (SEQ ID No. 21 and SEQ ID No. 23); (ii) 50 mM of a forward amplification primer (SEQ ID No. 26), 50 mM of a reverse amplification primer (SEQ ID No. 27), 50 mM of a reverse amplification primer (SEQ ID No. 28) and 100 nM of probes (SEQ ID No. 21 and SEQ ID No. 23); (iii) 50 mM of a forward amplification primer (SEQ ID No. 25), 50 mM of a reverse amplification primer (SEQ ID No. 27), 50 mM of a reverse amplification primer (SEQ ID No. 28) and 100 nM of probes (SEQ ID No. 21 and SEQ ID No. 23); (iv) 50 mM of a forward amplification primer (SEQ ID No. 25), 50 mM of a forward amplification primer (SEQ ID No. 26), 50 mM of a reverse amplification primer (SEQ ID No. 28) and 100 nM of probes (SEQ ID No. 21 and SEQ ID No. 23); (v) 50 mM of a forward amplification primer (SEQ ID No. 25), 50 mM of a forward amplification primer (SEQ ID No. 26), 50 mM of a reverse amplification primer (SEQ ID No. 28) and 100 nM of probes (SEQ ID No. 21 and SEQ ID No. 23); (vi) 50 mM of a forward amplification primer (SEQ ID No. 25), 50 mM of a forward amplification primer (SEQ ID No. 26), 50 mM of a reverse amplification primer (SEQ ID No. 27), 50 mM of a reverse amplification primer (SEQ ID No. 28) and 100 nM of probe (SEQ ID No. 23); or (vii) 50 mM of a forward amplification primer (SEQ ID No. 25), 50 mM of a forward amplification primer (SEQ ID No. 26), 50 mM of a reverse amplification primer (SEQ ID No. 27), 50 mM of a reverse amplification primer (SEQ ID No. 28) and 100 nM of probes (SEQ ID No. 21).

The total reaction volume was 20 microlitres with 5 microlitres of template nucleic acid extracted from Adenovirus added per reaction. Two different concentrations were tested.

The amplification cycles used were as follows: Hold for 600 seconds at 95 deg. C. with optics off; 95 deg. C. for 30 seconds with optics off and 55 deg. C. for 60 seconds with optics on (5 cycles); 95 deg. C. for 10 seconds with optics off and 55 deg. C. for 60 seconds (40 cycles) with optics on.

Results

Tables 5a-5d. Amplification and detection using different concentrations and combinations of primers and probes.

TABLE 5a

|  | SEQ ID Nos. 25, 26, 27, 28, 21 and 23 | | SEQ ID Nos. 26, 27, 28, 21 and 23 | |
| --- | --- | --- | --- | --- |
|  | $C_T$ | RFU | $C_T$ | RFU |
| Target($10^1$) | 38.5 | 240 | 39.2 | 143 |
| Target($10^3$) | 29.8 | 373 | 30.8 | 227 |

TABLE 5b

|  | SEQ ID Nos. 25, 27, 28, 21 and 23 | | SEQ ID Nos. 25, 26, 28, 21 and 23 | |
| --- | --- | --- | --- | --- |
|  | $C_T$ | RFU | $C_T$ | RFU |
| Target($10^1$) | 37.8 | 212 | 41.5 | 99 |
| Target($10^3$) | 30.2 | 275 | 32 | 258 |

TABLE 5c

|  | SEQ ID Nos. 25, 26, 27, 21 and 23 | | SEQ ID Nos. 25, 26, 27, 28 and 23 | |
| --- | --- | --- | --- | --- |
|  | $C_T$ | RFU | $C_T$ | RFU |
| Target($10^1$) | 41.8 | 96 | 37.7 | 254 |
| Target($10^3$) | 31.8 | 320 | 30 | 360 |

TABLE 5d

|  | SEQ ID Nos. 25, 26, 27, 28 and 21 | |
| --- | --- | --- |
|  | $C_T$ | RFU |
| Target ($10^1$) | 7.1 | 21 |
| Target ($10^3$) | 0 | 3 |

The results are presented as RFU values and represent the average of 6 experiments for each concentration.

Conclusion

Leaving out one of the primers or probes from the assay made little difference for the most part. However, omitting probe SEQ ID No. 23 resulted in lower detection in this particular experiment.

Example 6

Analysis of Primer and Probe Combinations for Detecting Adenovirus 18

Materials & Methods

The following reagents used: Fast Start Master Buffer (Roche) at 1× concentration, 3 Units of Fast Start Taq DNA polymerase (Roche), 150 nM forward amplification primers (SEQ ID No. 25 and SEQ ID No. 26) and 150 nM reverse amplification primers (SEQ ID No. 27 and SEQ ID No. 28) were used together with 300 nM probe (SEQ ID No. 29).

The total reaction volume was 20 microlitres with 5 microlitres of template nucleic acid extracted from Adenovirus 18 added per reaction. The amplification cycles used were as follows: Hold for 600 seconds at 95 deg. C. with optics off; 95 deg. C. for 30 seconds with optics off and 55 deg. C. for 60 seconds with optics on (5 cycles); 95 deg. C. for 10 seconds with optics off and 55 deg. C. for 60 seconds (40 cycles) with optics on.

Results

TABLE 6

Amplification and detection of Adenovirus 18.

| Serotype | $C_T$ | RFU |
|---|---|---|
| 18-6 | 17 | 1240 |
| 18-5 | 20 | 975 |
| 18-4 | 24 | 1242 |
| 18-3 | 30 | 1023 |
| 18-2 | 33 | 942 |
| 18-1 | 35 | 747 |
| 18-0 | 31 | 1215 |

The Serotype column is set-up to reflect "serotype number-$1\times10^x$ TCID$_{50}$/mL." $C_T$ values have all been rounded down. The results are presented as $C_T$/RFU values.

Conclusion

This combination of primers and probes successfully detects Adenovirus 18.

Example 7

Analysis of Further Primer and Probe Combinations for Detecting Adenovirus

Materials & Methods

The following reagents used: Fast Start Master Buffer (Roche) at 1× concentration, 3 Units of Fast Start Taq DNA polymerase (Roche), 150 nM forward amplification primers (SEQ ID No. 31 and SEQ ID No. 26) and 150 nM reverse amplification primers (SEQ ID No. 27 and SEQ ID No. 28) were used together with 150 nM probe (SEQ ID No. 21 and SEQ ID No. 23). The total reaction volume was 20 microlitres with 5 microlitres of template nucleic acid extracted from various Adenovirus serotypes added per reaction. The amplification cycles used were as follows: Hold for 600 seconds at 95 deg. C. with optics off; 95 deg. C. for 30 seconds with optics off and 55 deg. C. for 60 seconds with optics on (5 cycles); 95 deg. C. for 10 seconds with optics off and 55 deg. C. for 60 seconds (40 cycles) with optics on.

Results

TABLE 7

Primer and probe combinations for detecting various Adenovirus serotypes.

| Serotype | FAM | | Cy5 | |
|---|---|---|---|---|
| | $C_T$ | RFU | $C_T$ | RFU |
| 1 | 38.7 | 40 | 35.9 | 172 |
| 3 | 37.4 | 59 | 35.5 | 208 |
| 4 | 0 | 22 | 37.2 | 185 |
| 7 | 32.2 | 711 | 32 | 209 |
| 11 | 24.2 | 843 | 32.2 | 190 |
| 14 | 28.8 | 737 | 31.9 | 196 |
| 16 | 23.8 | 879 | 32.1 | 212 |
| 21 | 31.9 | 671 | 31.4 | 219 |
| 25 | 32.8 | 399 | 31.7 | 217 |
| 34 | 29.3 | 645 | 31.7 | 205 |
| 35 | 29.6 | 771 | 30.7 | 220 |
| 50 | 24.6 | 786 | 30.9 | 210 |

The results are presented as $C_T$/RFU values. The Fam-channel shows detection results for the template nucleic acids. The Cy5-channel shows detection results for an internal control nucleic acid.

Conclusion

With the exception of serotype 4, this combination of primers and probes successfully detected all of the serotypes tested.

Example 8

Analysis of Further Primer and Probe Combinations for Detecting Adenovirus

Materials & Methods

The following reagents used: Fast Start Master Buffer (Roche) at 1× concentration, 3 Units of Fast Start Taq DNA polymerase (Roche) and either: (i) 150 nM forward amplification primers (SEQ ID Nos. 33 and 34) and 150 nM reverse amplification primers (SEQ ID No. 27 and SEQ ID No. 28) were used together with 150 nM probe (SEQ ID No. 21 and SEQ ID No. 23); (ii) 150 nM forward amplification primers (SEQ ID Nos. 33 and 35) and 150 nM reverse amplification primers (SEQ ID No. 27 and SEQ ID No. 28) were used together with 150 nM probe (SEQ ID No. 21 and SEQ ID No. 23); or (iii) 150 nM forward amplification primers (SEQ ID Nos. 34 and 35) and 150 nM reverse amplification primers (SEQ ID No. 27 and SEQ ID No. 28) were used together with 150 nM probe (SEQ ID No. 21 and SEQ ID No. 23). The total reaction volume was 20 microlitres with 5 microlitres of template nucleic acid extracted from various Adenovirus serotypes added per reaction. The amplification cycles used were as follows: Hold for 600 seconds at 95 deg. C. with optics off; 95 deg. C. for 30 seconds with optics off and 55 deg. C. for 60 seconds with optics on (5 cycles); 95 deg. C. for 10 seconds with optics off and 55 deg. C. for 60 seconds (40 cycles) with optics on.

Results

Tables 8a-8c. Amplification and detection of various Adenovirus serotypes using combinations of primers and probes.

TABLE 8a

SEQ ID Nos. 33, 34, 27, 28, 21 and 23

| Serotype | FAM | | Cy5 | |
|---|---|---|---|---|
| | $C_T$ | RFU | $C_T$ | RFU |
| 1 | 35.6 | 318 | 35.9 | 243 |
| 3 | 37.3 | 87 | 35.8 | 210 |
| 4 | 36.9 | 150 | 35.6 | 232 |
| 19 | 38.1 | 95 | 35.2 | 217 |
| 31 | 35.7 | 247 | 34.6 | 257 |
| 41 | 36.7 | 244 | 35.9 | 285 |
| 14 | 29.7 | 868 | 31.5 | 250 |

TABLE 8b

SEQ ID Nos. 33, 35, 27, 28, 21 and 23

| Serotype | FAM | | Cy5 | |
|---|---|---|---|---|
| | $C_T$ | RFU | $C_T$ | RFU |
| 1 | 0 | 12 | 35.7 | 248 |
| 3 | 36.4 | 159 | 35.1 | 231 |
| 4 | 36.8 | 171 | 35.6 | 249 |
| 19 | 36.7 | 151 | 35.3 | 181 |
| 31 | 35.8 | 170 | 34.6 | 197 |
| 41 | 39.3 | 50 | 36 | 243 |
| 14 | 29.2 | 1062 | 31.5 | 256 |

TABLE 8c

SEQ ID Nos. 34, 35, 27, 28, 21 and 23

| Serotype | FAM | | Cy5 | |
|---|---|---|---|---|
| | $C_T$ | RFU | $C_T$ | RFU |
| 1 | 37.5 | 198 | 35.5 | 199 |
| 3 | 0 | 5 | 35.5 | 213 |
| 4 | 0 | 15 | 36.1 | 158 |
| 19 | 0 | 12 | 35.1 | 224 |
| 31 | 35.6 | 369 | 34.6 | 240 |
| 41 | 36.6 | 284 | 35.7 | 263 |
| 14 | 33.1 | 942 | 32.1 | 203 |

The results are presented as $C_T$ and RFU values. The Fam-channel shows detection results for the template nucleic acids. The Cy5-channel shows detection results for an internal control nucleic acid.

Conclusion

Table 8a of primers and probes successfully detected all of the serotypes tested. Tables 8b and 8c detected most serotypes tested.

Example 9

Analysis of Further Primer and Probe Combinations for Detecting Adenovirus

Materials & Methods

The following reagents used: Fast Start Master Buffer (Roche) at 1× concentration, 3 Units of Fast Start Taq DNA polymerase (Roche) and 150 nM forward amplification primers (SEQ ID Nos. 25 and 26) and 150 nM reverse amplification primers (SEQ ID No. 27 and SEQ ID No. 28) were used together with 150 nM probe (SEQ ID No. 36 and SEQ ID No. 37). The total reaction volume was 20 microlitres with 5 microlitres of template nucleic acid extracted from the Adenovirus 19 serotype positive control plasmid, which added per reaction at six different concentrations. The amplification cycles used were as follows: Hold for 600 seconds at 95 deg. C. with optics off; 95 deg. C. for 30 seconds with optics off and 55 deg. C. for 60 seconds with optics on (5 cycles); 95 deg. C. for 10 seconds with optics off and 55 deg. C. for 60 seconds (40 cycles) with optics on.

Results

TABLE 9

Amplification and detection of a serial dilution of target nucleic acid

| Concentration | FAM | |
|---|---|---|
| | $C_T$ | RFU |
| $10^4$ | 28.1 | 1127 |
| $10^4$ | 28.2 | 1040 |
| $10^4$ | 28 | 1196 |
| $10^3$ | 31.9 | 938 |
| $10^3$ | 32.1 | 922 |
| $10^3$ | 32.3 | 969 |
| $10^2$ | 35.3 | 865 |
| $10^2$ | 35.4 | 800 |
| $10^2$ | 35.2 | 800 |
| $10^1$ | 37.8 | 571 |
| $10^1$ | 33.6 | 59 |
| $10^1$ | 38.6 | 419 |
| $10^0$ | 0 | 10 |
| $10^0$ | 0 | 0 |
| $10^0$ | 0 | 0 |
| $10^{-1}$ | 0 | 0 |
| $10^{-1}$ | 0 | 0 |
| $10^{-1}$ | 0 | 0 |

The results are presented as $C_T$/RFU values.

Conclusion

These primers and probes successfully detected the control tested Adenovirus 19 serotype.

Example 10

Further Analysis of the Primer and Probe Combination from Example 9

Materials & Methods

The following reagents used: Fast Start Master Buffer (Roche) at 1× concentration, 3 Units of Fast Start Taq DNA polymerase (Roche) and 150 nM forward amplification primers (SEQ ID Nos. 25 and 26) and 150 nM reverse amplification primers (SEQ ID No. 27 and SEQ ID No. 28) were used together with 150 nM probe (SEQ ID No. 36 and SEQ ID No. 37). The total reaction volume was 20 microlitres with 5 microlitres of template nucleic acid extracted from various Adenovirus serotypes and tested at a concentration of $3 \times 10^0$. The amplification cycles used were as follows: Hold for 600 seconds at 95 deg. C. with optics off; 95 deg. C. for 30 seconds with optics off and 55 deg. C. for 60 seconds with optics on (5 cycles); 95 deg. C. for 10 seconds with optics off and 55 deg. C. for 60 seconds (40 cycles) with optics on.

Results

TABLE 10

Amplification and detection of Adenovirus target nucleic acids

| Serotype | $C_T$ | RFU |
|---|---|---|
| 2 | 31.6 | 1465 |
| 5 | 33.9 | 903 |
| 6 | 0 | 0 |

TABLE 10-continued

Amplification and detection of Adenovirus target nucleic acids

| Serotype | $C_T$ | RFU |
|---|---|---|
| 7 | 39 | 366 |
| 8 | 37.4 | 625 |
| 9 | 32 | 1223 |
| 10 | 36.3 | 837 |
| 11 | 26.6 | 950 |
| 12 | 31.8 | 1176 |
| 13 | 29.7 | 1487 |
| 14 | 34 | 671 |
| 15 | 33.5 | 1018 |
| 16 | 33.4 | 729 |
| 17 | 30.2 | 1622 |
| 18 | 40 | 175 |
| 20 | 27.2 | 1217 |
| 21 | 34.1 | 733 |
| 22 | 31.2 | 1150 |
| 23 | 30.1 | 1471 |
| 24 | 33.2 | 1110 |
| 25 | 37.3 | 661 |
| 26 | 29.1 | 1814 |
| 27 | 29.5 | 1637 |
| 28 | 34.2 | 1032 |
| 29 | 32.9 | 1159 |
| 30 | 28.4 | 1496 |
| 32 | 26.6 | 2079 |
| 33 | 33.9 | 1017 |
| 34 | 34.2 | 690 |
| 35 | 33.1 | 702 |
| 36 | 29.1 | 1312 |
| 37 | 30.2 | 1393 |
| 38 | 31.8 | 1202 |
| 39 | 30 | 1650 |
| 40 | 32.6 | 1290 |
| 42 | 29.1 | 1261 |
| 43 | 28.8 | 1832 |
| 44 | 23.3 | 1218 |
| 45 | 32.1 | 1289 |
| 46 | 32.5 | 1183 |
| 47 | 26.4 | 1209 |
| 48 | 29.4 | 1565 |
| 49 | 31.5 | 1264 |
| 50 | 32 | 846 |
| 51 | 31.4 | 1125 |

The results are presented as $C_T$ and RFU values.

Discussion

All of the serotypes tested were detected using this primer and probe concentration with the exception of serotype 6. This serotype was successfully detected at $3 \times 10^1$ $TCID_{50}$/mL and above.

Example 11

Exemplary Nucleic Acid Sequences

The instant example provides exemplary sequences that are useful with the present invention. This table does not limit the scope of the invention. Sequences are presented according to World Intellectual Property Organization (WIPO) Handbook on Industrial Property Information and Documentation, Standard ST.25 (1998), including Tables 1 through 6 of Appendix 2.

TABLE 11

Exemplary nucleic acid sequences

| SEQ ID No | Sequence 5' -> 3' |
|---|---|
| 1 | CAGGACGCCTCGGRGTAYCTSAG |
| 2 | GGAGCCACVGTGGGRTT |
| 3 | AAYCCCACBGTGGCTCC |
| 4 | CCGGGTCTGGTGCAGTTTGCCCGC |
| 5 | CACATCGCCGGACAGGA |
| 6 | CATACTGAAGTAGGTGTCTGT |
| 7 | ACAGACACCTACTTCAGTATG |
| 8 | CGGTGGTCACATCGTGG |
| 9 | CCACGATGTGACCACCG |
| 10 | AGTACCTCAGTCCGGGTCTGGTG |
| 11 | ATGGCTACCCCTTCGATG |
| 12 | ACCCCMTCGATGATGCC |
| 13 | GCGGGCGAATTGCACCA |
| 14 | TGGTGCAATTCGCCCGC |
| 15 | GCGGGCAAAYTGCACCA |
| 16 | TGGTGCARTTTGCCCGC |
| 17 | GACTCAGGTACTCCGAAGCATCCT |
| 18 | AGGATGCTTCGGAGTACCTGAGTC |
| 19 | CTCAGGTACTCCGAGGCGTCCT |
| 20 | AGGACGCCTCGGAGTACCTGAG |
| 21 | CTCAGGTACTCCGAAGCATCCT |
| 22 | AGGATGCTTCGGAGTACCTGAG |
| 23 | CAGGTACTCCGAGGCGTCCT |
| 24 | AGGACGCCTCGGAGTACCTG |
| 25 | ACCCCATCGATGATGCC |
| 26 | ACCCCCTCGATGATGCC |
| 27 | GCGGGCAAACTGCACCA |
| 28 | GCGGGCAAATTGCACCA |
| 29 | CTCAGGTATTCCGAGGCATCCT |
| 30 | AGGATGCCTCGGAATACCTGAG |
| 31 | ACCCCATCGATGCTGCC |
| 32 | ACCCCATCGATGATGCC |
| 33 | TGGGCGTACATGCACATC |
| 34 | GTGGTCTTACATGCACATC |
| 35 | GTGGGCATACATGCACATC |
| 36 | AGGATGCTTCGGAGTACCTGAG |
| 37 | AGGACGCCTCGGAGTACCTG |
| 38 | ARTGGKCDTACATGCACATC |

TABLE 11-continued

Exemplary nucleic acid sequences

| SEQ ID No | Sequence 5' -> 3' |
|---|---|
| 39 | CAGGACGCCTCGGAGTACCT |
| 40 | AGGATGCTTCGGAGTACCTGAG |
| 41 | CACGATGTGACCACAGA |
| 42 | CAYGATGTGACCACAGA |
| 43 | CACGAYGTGACCACAGA |
| 44 | CACGATGTGACCACSGA |
| 45 | CACGATGTGACCACVGA |
| 46 | CAYGAYGTGACCACVGA |

Human adenovirus 9 gene for hexon, complete cds, strain: Hicks. GenBank Accession Number AB330090.1 and gi number GI:190356540. First seen at NCBI on Jun. 13, 2008. (SEQ ID NO:47)

atggccacccctcgatgatgccgcagtgggcgtacatgcacatcgccgg
gcaggacgcctcggagtacctgagcccgggtctggtgcagtttgcccgcg
ccaccgacacgtacttcagcctgggcaacaagtttaggaaccccacggtg
gccccgacccacgatgtgaccacggaccggtcccagcgtctgacgctgcg
cttcgtgcccgtggatcgcgaggacaccacgtactcgtacaaggcgcgct
tcactctggccgtgggcgacaaccgggtgctagacatggccagcacttac
tttgacatccgcggcgtcctggaccgcggtcccagcttcaaaccctactc
gggcacagcttacaacagtctggcccccaagggtgcccccaactccagcc
agtggcttgcaaaagacaccaatgctggcgatcaagcattaaaaacccac
acacatggcgtagctgctatgggggaacagatatcacagcaaagggttt
gcaaattggtgttgacacgactgaaaacaagaatgagcctatttatgcaa
atgaaatataccagccagaacctcaggtaggagaggaaaacttgcaagat
gttgaaaacttttatggaggcagagctcttaaaaaagaaaccaaaatgaa
accttgctatggctcgtttgccagacccacaaatgaaaaaggcggtcaag
ccaaattttaactgacggcgatggtcagctaactaaaaatcatgatatc
acaatgaatttctttgacactcctggaggaacagttggtcaggatactga
acttgaagcagacattgttatgtatgctgagaatgtgcatctggaaactc
cagacacgcatgtggtgtacaaaccaggaacttctgatgagagttcagaa
gcaaatttggttcagcagtccatgccaaacaggcccaactacatcggctt
cagggacaactttgtgggtctcatgtactataacagcactggcaacatgg
gtgtgctggctggtcaagcatctcagttgaatgctgtggtcgacttgcaa
gacagaaacacagagctgtcttaccagctcttgctagattctctgggtga
cagaaccagatactttagcatgtggaactctgcagtggacagttatgatc
ctgatgtcaggattattgaaaatcacggtgtggaagatgaacttccaaac
tattgcttcccattggatggagctggcactaatgctacctaccaaggtgt
aaaagttaaaaatggccaagatggagatgtaaacgcagattgggaaaag atccaaatcttgcttcacgaaaccaaatatgcaagggtaacatcttcgcc
atggagatcaacctccaggccaacctgtggaagagttttctgtactcgaa
tgtggccctgtacctgcccgactcatacaagtacacgccggccaacgtca
cgctgcccgccaataccaacacctacgagtacatgaacggccgcgtggta
gccccctcgctggtggacgcctacatcaacatcggcgcccggtggtcgct
ggacccatggacaacgtcaacccattcaaccaccaccgcaacgcgggcc
tgcgttaccgctccatgcttctgggcaacggccgctacgtgcccttccac
atccaagtgccccaaaagttcttttgccatcaagaacctgctcctgctccc
cggctcctacacctacgagtggaacttccgcaaggatgtcaacatgatcc
tgcagagttccctcggaaacgacctgcgcgtcgacggcgcctccgtccgc
ttcgacagcgtcaacctctacgccacattcttccccatggcgcacaacac
cgcctccaccctggaagccatgctgcgcaacgacaccaacgaccagtcct
tcaacgactacctctcggccgccaacatgctctaccccatcccggccaag
gccaccaacgtgcccatctccatccctcgcgcaactgggccgccttccg
cggctggagtttcacccggctcaagaccaaagaaactccctccctcggct
cgggtttcgatccctactttgtatactcgggttccatccctacctcgac
gggaccttctacctcaaccacaccttcaagaaggtctccatcatgttcga
ctcctcggtcagctggcccggcaacgaccggctgctcacgccgaacgagt
tcgagatcaagcgcagtgtcgacggggagggctacaatgtggcccaatgc
aacatgaccaaggactggttcctcgtccagatgctctcccactacaacat
cggctaccagggcttccacgtgcccgagggctacaaggaccgcatgtact
ccttcttccgcaacttccagcccatgagcaggcaggtggtcgatgagatc
aactacaaggactacaaggccgtcaccctgcccttccagcacaacaactc
gggcttcaccggctaccttgcacccaccatgcgtcaggggcagccctacc
ccgccaacttcccctatcctctcatcggccagacagccgtgccctctgtc
acccagaaaaagttcctctgcgacagggtcatgtggcgcatccccttctc
cagcaacttcatgtccatgggcgcccctcaccgacctgggtcagaacatgc
tctatgccaactcggcccacgcgctcgacatgaccttcgaggtggacccc
atggatgagcccaccctcctctatcttctcttcgaagttttcgacgtggt
cagagtgcaccagccgcaccgcggcgtcatcgaggccgtctacctgcgca
cgcccttctccgccggcaacgccaccacctaa The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

The methods illustratively described herein may suitably be practiced in the absence of any element or elements, limitation or limitations, not specifically disclosed herein. Thus, for example, the terms "comprising", "including,"

containing", etc. shall be read expansively and without limitation. Additionally, the terms and expressions employed herein have been used as terms of description and not of limitation, and there is no intention in the use of such terms and expressions of excluding any equivalents of the features shown and described or portions thereof. It is recognized that various modifications are possible within the scope of the invention claimed. Thus, it should be understood that although the present invention has been specifically disclosed by preferred embodiments and optional features, modification and variation of the invention embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the methods. This includes the generic description of the methods with a proviso or negative limitation removing any subject matter from the genus, regardless of whether or not the excised material is specifically recited herein.

Other embodiments are within the following claims. In addition, where features or aspects of the methods are described in terms of Markush groups, those skilled in the art will recognize that the invention is also thereby described in terms of any individual member or subgroup of members of the Markush group.

We claim:

1. A method for specifically detecting an Adenovirus target nucleic acid in a sample comprising the steps of:
   (a) contacting a sample suspected of containing at least an Adenovirus nucleic acid with at least two amplification oligomers for generating an amplicon, wherein each of said at least two amplification oligomers is from 10 to 50 nucleotides in length and wherein the amplification oligomers are respectively configured to specifically hybridize to regions within a target sequence of Adenovirus selected from the group consisting of from nucleotides 1 to 99 and from nucleotides 83 to 175 of Accession Number AB330090.1 (SEQ ID NO: 47), wherein
      at least one of said at least two amplification oligomers is complementary to the targeted Adenovirus nucleic acid within nucleotides 1 to 99 of SEQ ID NO: 47 and comprises or consists of a target hybridizing sequence as set forth in SEQ ID NO: 25 with no mismatches or with 1 or 2 mismatches to the targeted Adenovirus nucleic acid; and
      at least one of said at least two amplification oligomers is complementary to the targeted Adenovirus nucleic acid within nucleotides 83 to 175 of SEQ ID NO: 47 and comprises or consists of a target hybridizing sequence as set forth in SEQ ID NO: 27 with no mismatches or with 1 or 2 mismatches to the targeted Adenovirus nucleic acid;
   (b) providing conditions sufficient for generating an amplicon from an Adenovirus target nucleic acid present in said sample using said amplification oligomers from step (a); and
   (c) providing conditions for detecting said amplicon and determining whether an Adenovirus target nucleic acid is present in said sample.

2. The method of claim 1, wherein at least one first amplification oligomer comprises or consists of a target hybridizing sequence as set forth in SEQ ID NO:25 and/or 26 and at least one second amplification oligomer comprises or consists of a target hybridizing sequence as set forth in SEQ ID NO: 27 and/or 28; or
   wherein at least two first amplification oligomers each respectively comprises or consists of the target hybridizing sequence as set forth in SEQ ID NO:25 and 26 and at least two second amplification oligomers each respectively comprises or consists of a target hybridizing sequence as set forth in SEQ ID NO: 27 and 28.

3. The method of claim 2, wherein the combination of amplification oligomers is SEQ ID NOs: 25, 26, 27 and 28; or SEQ ID NOs: 26, 27 and 28; or SEQ ID NOs: 25, 26 and 28; or SEQ ID NOs: 25, 26 and 27; or SEQ ID NOs: 25, 27 and 28; or SEQ ID NOs: 25 and 27; or SEQ ID NOs: 25 and 28; or SEQ ID NOs: 26 and 27; or SEQ ID NOs: 26 and 28.

4. The method of claim 1, wherein said detection step comprises contacting said amplification product with at least one detection probe configured to hybridize to a portion of said amplification product.

5. The method according to claim 4, wherein the detection probe comprises or consists of a target hybridizing sequence selected from the group consisting of SEQ ID NOs: 10, 17, 19, 21, 23, 24, 29, 36 and 37 or a combination of two or more thereof.

6. The method according to claim 4, wherein the detection probe comprises a sequence consisting of SEQ ID NO: 36 and/or SEQ ID NO: 37.

7. The method of claim 2, wherein said detection step comprises contacting said amplification product with at least one detection probe configured to hybridize to a portion of said amplification product, wherein the detection probe comprises or consists of a target hybridizing sequence selected from the group consisting of SEQ ID NOs: 10, 17, 19, 21, 23, 24, 29, 36 and 37 or a combination of two or more thereof.

8. The method of claim 7, wherein the detection probe comprises a sequence consisting of SEQ ID NO: 36 and/or SEQ ID NO: 37.

9. The method of claim 3, wherein said detection step comprises contacting said amplification product with at least one detection probe configured to hybridize to a portion of said amplification product, wherein the detection probe comprises or consists of a target hybridizing sequence selected from the group consisting of SEQ ID NOs: 10, 17, 19, 21, 23, 24, 29, 36 and 37 or a combination of two or more thereof.

10. The method of claim 9, wherein the detection probe comprises a sequence consisting of SEQ ID NO: 36 and/or SEQ ID NO: 37.

11. A composition for use in an Adenovirus target nucleic acid amplification and detection assay comprising (i) at least two amplification oligomers capable of stably hybridizing to Adenovirus target nucleic acid and (ii) a detection probe capable of stably hybridizing to an amplicon generated by said at least two amplification oligomers,
wherein each of said at least two amplification oligomers is from 10 to 50 nucleotides in length and wherein the amplification oligomers are respectively configured to specifically hybridize to regions within a target sequence of Adenovirus selected from the group consisting of from nucleotides 1 to 99 and from nucleotides 83 to 175 of Accession Number AB330090.1 (SEQ ID NO: 47) wherein,
at least one of said at least two amplification oligomers is complementary to the targeted Adenovirus nucleic acid within nucleotides 1 to 99 of SEQ ID NO: 47 and comprises or consists of a target hybridizing sequence as set forth in SEQ ID NO: 25 with no mismatches or with 1 or 2 mismatches to the targeted Adenovirus nucleic acid; and
at least one of said at least two amplification oligomers is complementary to the targeted Adenovirus nucleic acid within nucleotides 83 to 175 of SEQ ID NO: 47 and comprises or consists of a target hybridizing sequence as set forth in SEQ ID NO: 27 with no mismatches or with 1 or 2 mismatches to the targeted Adenovirus nucleic acid; and
wherein the detection probe comprises a fluorescent or chemiluminescent label.

12. The composition according to claim 11, wherein at least one first amplification oligomer comprises or consists of a target hybridizing sequence as set forth in SEQ ID NO:25 and/or SEQ ID NO:26 and wherein at least one second amplification oligomer comprises or consists of a target hybridizing sequence as set forth in SEQ ID NO:27 and/or SEQ ID NO:28.

13. The composition according to claim 12, wherein the first and second amplification oligomers are selected from the group consisting of SEQ ID NOs: 25, 26, 27 and 28; SEQ ID NOs: 26, 27 and 28; SEQ ID NOs: 25, 26 and 28; SEQ ID NOs: 25, 26 and 27; SEQ ID NOs: 25, 27 and 28; SEQ ID NOs: 25 and 27; SEQ ID NOs: 25 and 28; SEQ ID NOs: 26 and 27 and SEQ ID NOs: 26 and 28 or a combination of two or more thereof.

14. The composition of claim 11, wherein the detection probe comprises the fluorescent label in combination with a quencher.

15. The composition according to claim 14, wherein the detection probe comprises or consists of a sequence selected from the group consisting of SEQ ID NOs: 10, 17, 19, 21, 23 24, 29, 36 and 37 or a combination of two or more thereof; preferably wherein the detection probe comprises or consists of a sequence as set forth in SEQ ID NO: 36 and/or SEQ ID NO: 7.

16. The composition of claim 12, further comprising a wherein the detection probe comprises the fluorescent label in combination with a quencher.

17. The composition according to claim 16, wherein the detection probe comprises or consists of a sequence selected from the group consisting of SEQ ID NOs: 10, 17, 19, 21, 23 24, 29, 36 and 37 or a combination of two or more thereof; preferably wherein the detection probe comprises or consists of a sequence as set forth in SEQ ID NO: 36 and/or SEQ ID NO: 37.

18. The composition of claim 13, wherein the detection probe comprises the fluorescent label in combination with a quencher.

19. The composition according to claim 18, wherein the detection probe comprises or consists of a sequence selected from the group consisting of SEQ ID NOs: 10, 17, 19, 21, 23 24, 29, 36 and 37 or a combination of two or more thereof; preferably wherein the detection probe comprises or consists of a sequence as set forth in SEQ ID NO: 36 and/or SEQ ID NO: 37.

20. A kit comprising the composition claim 11 and optionally a set of instructions for performing same.

* * * * *

```
                            SEQUENCE LISTING

<160> NUMBER OF SEQ ID NOS: 47

<210> SEQ ID NO 1
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 1
caggacgcct cggrgtayct sag                                              23

<210> SEQ ID NO 2
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 2
ggagccacvg tgggrtt                                                     17

<210> SEQ ID NO 3
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 3
aaycccacbg tggctcc                                                     17

<210> SEQ ID NO 4
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 4
ccgggtctgg tgcagtttgc ccgc                                             24

<210> SEQ ID NO 5
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 5
cacatcgccg gacagga                                                     17
```

-continued

<210> SEQ ID NO 6
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 6
catactgaag taggtgtctg t                                              21

<210> SEQ ID NO 7
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 7
acagacacct acttcagtat g                                              21

<210> SEQ ID NO 8
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 8
cggtggtcac atcgtgg                                                   17

<210> SEQ ID NO 9
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 9
ccacgatgtg accaccg                                                   17

<210> SEQ ID NO 10
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 10
agtacctcag tccgggtctg gtg                                            23

<210> SEQ ID NO 11
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 11
atggctaccc cttcgatg                                                  18

<210> SEQ ID NO 12
<211> LENGTH: 17
<212> TYPE: DNA
<213> ORGANISM: Artificial Sequence
<220> FEATURE:

```
<223> OTHER INFORMATION: Synthetic Oligonucleotide

<400> SEQUENCE: 12
accccmtcga tgatgcc                                                      17

<210> SEQ ID NO 13
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 13
gcgggcgaat tgcacca                                                      17

<210> SEQ ID NO 14
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 14
tggtgcaatt cgcccgc                                                      17

<210> SEQ ID NO 15
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 15
gcgggcaaay tgcacca                                                      17

<210> SEQ ID NO 16
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 16
tggtgcartt tgcccgc                                                      17

<210> SEQ ID NO 17
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 17
gactcaggta ctccgaagca tcct                                              24

<210> SEQ ID NO 18
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 18
aggatgcttc ggagtacctg agtc                                              24
```

```
<210> SEQ ID NO 19
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 19
ctcaggtact ccgaggcgtc ct                                          22

<210> SEQ ID NO 20
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 20
aggacgcctc ggagtacctg ag                                          22

<210> SEQ ID NO 21
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 21
ctcaggtact ccgaagcatc ct                                          22

<210> SEQ ID NO 22
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 22
aggatgcttc ggagtacctg ag                                          22

<210> SEQ ID NO 23
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 23
caggtactcc gaggcgtcct                                             20

<210> SEQ ID NO 24
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 24
aggacgcctc ggagtacctg                                             20

<210> SEQ ID NO 25
<211> LENGTH: 17
<212> TYPE: DNA
<213> ORGANISM: Artificial Sequence
<220> FEATURE:
<223> OTHER INFORMATION: Synthetic Oligonucleotide
```

```
<400> SEQUENCE: 25
accccatcga tgatgcc                                                     17

<210> SEQ ID NO 26
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 26
accccctcga tgatgcc                                                     17

<210> SEQ ID NO 27
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 27
gcgggcaaac tgcacca                                                     17

<210> SEQ ID NO 28
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 28
gcgggcaaat tgcacca                                                     17

<210> SEQ ID NO 29
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 29
ctcaggtatt ccgaggcatc ct                                               22

<210> SEQ ID NO 30
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 30
aggatgcctc ggaatacctg ag                                               22

<210> SEQ ID NO 31
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 31
accccatcga tgctgcc                                                     17

<210> SEQ ID NO 32
<211> LENGTH: 17
```

```
<212> TYPE: DNA
<213> ORGANISM: Artificial Sequence
<220> FEATURE:
<223> OTHER INFORMATION: Synthetic Oligonucleotide

<400> SEQUENCE: 32
accccatcga tgatgcc                                                 17

<210> SEQ ID NO 33
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 33
tgggcgtaca tgcacatc                                                18

<210> SEQ ID NO 34
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 34
gtggtcttac atgcacatc                                               19

<210> SEQ ID NO 35
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 35
gtgggcatac atgcacatc                                               19

<210> SEQ ID NO 36
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 36
aggatgcttc ggagtacctg ag                                           22

<210> SEQ ID NO 37
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 37
aggacgcctc ggagtacctg                                              20

<210> SEQ ID NO 38
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 38
```

```
artggkcdta catgcacatc                                               20

<210> SEQ ID NO 39
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 39
caggacgcct cggagtacct                                               20

<210> SEQ ID NO 40
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 40
aggatgcttc ggagtacctg ag                                            22

<210> SEQ ID NO 41
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 41
cacgatgtga ccacaga                                                  17

<210> SEQ ID NO 42
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 42
caygatgtga ccacaga                                                  17

<210> SEQ ID NO 43
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 43
cacgaygtga ccacaga                                                  17

<210> SEQ ID NO 44
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 44
cacgatgtga ccacsga                                                  17

<210> SEQ ID NO 45
<211> LENGTH: 17
<212> TYPE: DNA
<213> ORGANISM: Artificial Sequence
```

```
<220> FEATURE:
<223> OTHER INFORMATION: Synthetic Oligonucleotide

<400> SEQUENCE: 45
cacgatgtga ccacvga                                                        17

<210> SEQ ID NO 46
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 46
caygaygtga ccacvga                                                        17

<210> SEQ ID NO 47
<211> LENGTH: 2832
<212> TYPE: DNA
<213> ORGANISM: Human adenovirus

<400> SEQUENCE: 47
atggccaccc cctcgatgat gccgcagtgg gcgtacatgc acatcgccgg gcaggacgcc          60
tcggagtacc tgagcccggg tctggtgcag tttgcccgcg ccaccgacac gtacttcagc         120
ctgggcaaca gtttaggaa ccccacggtg gccccgaccc acgatgtgac cacggaccgg          180
tcccagcgtc tgacgctgcg cttcgtgccc gtggatcgcg aggacaccac gtactcgtac         240
aaggcgcgct tcactctggc cgtgggcgac aaccgggtgc tagacatggc cagcacttac         300
tttgacatcc gcggcgtcct ggaccgcggt cccagcttca accctactc gggcacagct          360 tacaacagtc tggcccccaa gggtgccccc aactccagcc agtggcttgc aaaagacacc         420
aatgctggcg atcaagcatt aaaaacccac acacatggcg tagctgctat gggggaaca          480 gatatcacag caaagggttt gcaaattggt gttgacacga ctgaaaacaa gaatgagcct         540
atttatgcaa atgaaatata ccagccagaa cctcaggtag agaggaaaa cttgcaagat          600 gttgaaaact tttatggagg cagagctctt aaaaaagaaa ccaaaatgaa accttgctat         660
ggctcgtttg ccagacccac aaatgaaaaa ggcggtcaag ccaaattttt aactgacggc         720
gatggtcagc taactaaaaa tcatgatatc acaatgaatt tctttgacac tcctggagga         780
acagttggtc aggatactga acttgaagca gacattgtta tgtatgctga aatgtgcat          840 ctggaaactc cagacacgca tgtggtgtac aaaccaggaa cttctgatga gagttcagaa         900
gcaaatttgg ttcagcagtc catgccaaac aggcccaact catcggctt cagggacaac         960 tttgtgggtc tcatgtacta aacagcact ggcaacatgg gtgtgctggc tggtcaagca        1020
tctcagttga atgctgtggt cgacttgcaa gacagaaaca cagagctgtc ttaccagctc        1080
ttgctagatt ctctgggtga cagaaccaga tactttagca tgtggaactc tgcagtggac        1140
agttatgatc ctgatgtcag gattattgaa atcacggtg tggaagatga acttccaaac         1200
tattgcttcc cattggatgg agctggcact aatgctacct accaaggtgt aaaagttaaa        1260
aatggccaag atgagatgt aaacgcagat tgggaaaaag atccaaatct tgcttcacga         1320
aaccaaatat gcaagggtaa catcttcgcc atggagatca acctccaggc caacctgtgg        1380
aagagttttc tgtactcgaa tgtggccctg tacctgccccg actcatacaa gtacacgccg        1440
gccaacgtca cgctgcccgc caataccaac acctacgagt acatgaacgg ccgcgtggta        1500
gccccctcgc tggtggacgc ctacatcaac atcggcgccc ggtggtcgct ggaccccatg        1560
```

-continued

```
gacaacgtca acccattcaa ccaccaccgc aacgcgggcc tgcgttaccg ctccatgctt    1620
ctgggcaacg gccgctacgt gcccttccac atccaagtgc cccaaaagtt ctttgccatc    1680
aagaacctgc tcctgctccc cggctcctac acctacgagt ggaacttccg caaggatgtc    1740
aacatgatcc tgcagagttc cctcggaaac gacctgcgcg tcgacggcgc ctccgtccgc    1800
ttcgacagcg tcaacctcta cgccacattc ttccccatgg cgcacaacac cgcctccacc    1860
ctggaagcca tgctgcgcaa cgacaccaac gaccagtcct tcaacgacta cctctcggcc    1920
gccaacatgc tctaccccat cccggccaag gccaccaacg tgcccatctc catccctcg     1980 cgcaactggg ccgccttccg cggctggagt ttcacccgc tcaagaccaa agaaactccc     2040
tccctcggct cgggtttcga tccctacttt gtatactcgg gttccatccc ctacctcgac    2100
gggaccttct acctcaacca caccttcaag aaggtctcca tcatgttcga ctcctcggtc    2160
agctggcccg gcaacgaccg gctgctcacg ccgaacgagt tcgagatcaa gcgcagtgtc    2220
gacggggagg gctacaatgt ggcccaatgc aacatgacca aggactggtt cctcgtccag    2280
atgctctccc actacaacat cggctaccag ggcttccacg tgcccgaggg ctacaaggac    2340
cgcatgtact ccttcttccg caacttccag cccatgagca ggcaggtggt cgatgagatc    2400
aactacaagg actacaaggc cgtcaccctg cccttccagc acaacaactc gggcttcacc    2460
ggctaccttg cacccaccat gcgtcagggg cagccctacc ccgccaactt cccctatcct    2520
ctcatcggcc agacagccgt gccctctgtc acccagaaaa agttcctctg cgacagggtc    2580
atgtggcgca tccccttctc cagcaacttc atgtccatgg gcgccctcac cgacctgggt    2640
cagaacatgc tctatgccaa ctcggcccac gcgctcgaca tgaccttcga ggtggacccc    2700
atggatgagc ccaccctcct ctatcttctc ttcgaagttt tcgacgtggt cagagtgcac    2760
cagccgcacc gcggcgtcat cgaggccgtc tacctgcgca cgcccttctc cgccggcaac    2820
gccaccacct aa                                                        2832
```